US012788813B2

(12) United States Patent
June et al.

(10) Patent No.: US 12,788,813 B2
(45) **Date of Patent: *Nov. 10, 2026**

(54) TOXICITY MANAGEMENT FOR ANTI-TUMOR ACTIVITY OF CARS

(71) Applicants: The Trustees of the University of Pennsylvania, Philadelphia, PA (US); The Children's Hospital of Philadelphia, Philadelphia, PA (US)

(72) Inventors: Carl H. June, Merion Station, PA (US); Bruce L. Levine, Cherry Hill, NJ (US); Michael D. Kalos, Philadelphia, PA (US); Stephan Grupp, Havertown, PA (US)

(73) Assignees: The Trustees of the University of Pennsylvania, Philadelphia, PA (US); The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/413,358

(22) Filed: Dec. 9, 2025

(65) Prior Publication Data

US 2026/0115284 A1 Apr. 30, 2026

Related U.S. Application Data

(63) Continuation of application No. 19/233,446, filed on Jun. 10, 2025, now abandoned, which is a continuation of application No. 18/937,759, filed on Nov. 5, 2024, now abandoned, which is a continuation of application No. 17/677,208, filed on Feb. 22, 2022, now abandoned, which is a continuation of application No. 15/963,728, filed on Apr. 26, 2018, now Pat. No. 11,273,219, which is a continuation of application No. 14/410,659, filed as application No. PCT/US2013/050267 on Jul. 12, 2013, now abandoned.

(60) Provisional application No. 61/782,982, filed on Mar. 14, 2013, provisional application No. 61/671,482, filed on Jul. 13, 2012.

(51) Int. Cl.

| | |
|---|---|
| ***A61P 35/02*** | (2006.01) |
| ***A61K 31/7088*** | (2006.01) |
| ***A61K 31/713*** | (2006.01) |
| ***A61K 35/00*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61K 48/00*** | (2006.01) |
| ***C12Q 1/6886*** | (2018.01) |
| ***G01N 33/68*** | (2006.01) |
| *A61K 39/00* | (2006.01) |

(52) U.S. Cl.

CPC ...... *A61K 39/3955* (2013.01); *A61K 31/7088* (2013.01); *A61K 31/713* (2013.01); *A61K 35/00* (2013.01); *A61K 40/11* (2025.01); *A61K 40/31* (2025.01); *A61K 40/4211* (2025.01); *A61K 45/06* (2013.01); *A61K 48/0083* (2013.01); *C12Q 1/6886* (2013.01); *G01N 33/6803* (2013.01); *A61K 2039/505* (2013.01); *A61K 2039/515* (2013.01); *A61K 2239/38* (2023.05); *A61K 2239/48* (2023.05); *G01N 33/6863* (2013.01); *G01N 2333/52* (2013.01); *G01N 2800/52* (2013.01)

(58) Field of Classification Search

CPC .................... A61K 40/11; A61K 40/31; A61K 2039/505; A61P 35/02; A61P 37/06; A61P 39/02

See application file for complete search history.

(56) References Cited

U.S. PATENT DOCUMENTS

| | | | |
|---|---|---|---|
| 5,199,942 | A | 4/1993 | Gillis |
| 5,225,539 | A | 7/1993 | Winter |
| 5,530,101 | A | 6/1996 | Queen et al. |
| 5,585,089 | A | 12/1996 | Queen et al. |
| 5,693,761 | A | 12/1997 | Queen et al. |

(Continued)

FOREIGN PATENT DOCUMENTS

| | | | |
|---|---|---|---|
| AU | 2008207646 | A1 | 9/2008 |
| JP | 2007505127 | A | 3/2007 |

(Continued)

OTHER PUBLICATIONS

Bugelski (2009, Expert Review of Clinical Immunology, 5:499-521).*

Actemra Highlights of Prescribing Information.

Adusumilli, et al., Abstract CT036: A phase I clinical trial of malignant pleural disease treated with regionally delivered autologous mesotheli•• targeted CAR T cells: Safety and efficacy, Cancer Research, 79(Suppl._13), 1-2, Jul. 1, 2019.

(Continued)

*Primary Examiner* — Valerie E Bertoglio

(74) *Attorney, Agent, or Firm* — Saul Ewing LLP; Kathryn Doyle; Valerie O'Shea Murray

(57) ABSTRACT

The present invention provides compositions and methods for treating cancer in a patient. In one embodiment, the method comprises a first-line therapy comprising administering to a patient in need thereof a genetically modified T cell expressing a CAR wherein the CAR comprises an antigen binding domain, a transmembrane domain, a costimulatory signaling region, and a CD3 zeta signaling domain and monitoring the levels of cytokines in the patient post T cell infusion to determine the type of second-line of therapy appropriate for treating the patient as a consequence of the presence of the CAR T cell in the patient.

6 Claims, 18 Drawing Sheets

Specification includes a Sequence Listing.

(56) References Cited

U.S. PATENT DOCUMENTS

| | | | |
|---|---|---|---|
| 5,693,762 A | 12/1997 | Queen et al. | |
| 6,267,722 B1 | 7/2001 | Anderson et al. | |
| 6,656,745 B1 | 12/2003 | Cole | |
| 6,818,455 B2 | 11/2004 | May et al. | |
| 7,189,522 B2 | 3/2007 | Esfandiari | |
| 10,603,378 B2 * | 3/2020 | June | A61P 37/06 |
| 11,273,219 B2 * | 3/2022 | June | A61P 35/02 |
| 2006/0251653 A1 | 11/2006 | Okuda et al. | |
| 2009/0004189 A1 | 1/2009 | Behrens | |
| 2009/0325167 A1 | 12/2009 | Chappell et al. | |
| 2010/0150829 A1 | 6/2010 | Garcia-Martinez et al. | |
| 2010/0273797 A1 | 10/2010 | Boman et al. | |

FOREIGN PATENT DOCUMENTS

| | | |
|---|---|---|
| WO | 9007861 A1 | 7/1990 |
| WO | 9117271 A1 | 11/1991 |
| WO | 9201047 A1 | 1/1992 |
| WO | 9312227 A1 | 6/1993 |
| WO | 2005023761 A2 | 3/2005 |
| WO | 2008144763 A2 | 11/2008 |
| WO | 2010065072 A1 | 6/2010 |
| WO | 2010075249 A1 | 7/2010 |
| WO | 2011066371 A2 | 6/2011 |
| WO | 2012079000 A1 | 6/2012 |
| WO | 2013033626 A2 | 3/2013 |
| WO | 2014011984 A1 | 1/2014 |

OTHER PUBLICATIONS

Against All Odds, by Tom Whitehead, as told to Jo Cavallo, Jan. 25, 2018, The ASCO Post—Transcript of online article. Article available online at: https://ascopost.com/issues/january-25-2018/against-all-odds.

Aggarwal, et al., Methotrexate inhibits interleukin-6 production in patients with juvenile rheumatoid arthritis, Rheumatology International, 23, 134-137, Mar. 7, 2023.

Aggarwal, et al., Rituximab, Anti-CD20, Induces In Vivo Cytokine Release But Does Not Impair Ex Vivo T-Cell Responses, American Journal of Transplantation, 4, 1357-1360, 2004.

Alten, Tocilizumab: a novel humanized anti . . . interleukin 6 receptor antibody for the treatment of patients with rheumatoid arthritis, Therapeutic Advances in Musculoskeletal Disease, 3(3), 133-149, 2011.

Anurathapan, et al., Engineered T cells for cancer treatment, Cytotherapy, 16, 713-733, 2014.

Applicant submission of Aug. 8, 2016, in European Patent Application No. 13817210.1.

Applicant submission of Jun. 26, 2019, in European Patent Application No. 13817210.1.

Bargou, et al., Tumor regression in cancer patients by very low doses of a T cell-engaging antibody, Science, 321, 974-977, Aug. 15, 2008.

Barnes, Corticosteroid effects on cell signalling, European Respiratory Journal, 27(2), 413-426, 2006.

Barrett, et al., Bone Marrow Transplants from HLA-Identical Siblings as Compared with Chemotherapy for Children ,vith Acute Lymphoblastic Leukemia in a Second Remission, The New England Journal of Medicine, 331(19), 1253-1258, Nov. 10, 1994.

Behrens, et al., Repeated TLR9 stimulation results in macrophage activation syndrome-like disease in mice, Journal of Clinical Investigation, 121(6), 2264-2277, Jun. 2011.

Bierer, et al., Cyclosporin A and FK506: molecular mechanisms of immunosuppression and probes for transplantation biology, Current Opinion in Immunology, 5, 763-773, 1993.

Bird, et al., Single-Chain Antigen-Binding Proteins, Science, 242, 423-426, Oct. 21, 1988.

Boye, et al., An overview of the current clinical use of the anti-CD20 monoclonal antibody rituximab, Annals of Oncology, 14, 520-535, 2003.

Brandl, et al., The effect of dexamethasone on polyclonal T cell activation and redirected target cell lysis as induced by a CD19/CD3- bispecific single-chain antibody construct, Cancer Immunology Immunotherapy, 56, 1551-1563, Feb. 20, 2007.

Brattsand, et al., Cytokine modulation by glucocorticoids: mechanisms and actions in cellular studies, Alimentary Pharmacology and Therapeutics, 10(2), 81-90, 1996.

Brennan, et al., Safety and immunotoxicity assessment of immunomodulatory monoclonal antibodies, mAbs, 2(3), 233-255, May 1, 2010.

Brentjens, et al., Safety and persistence of adoptively transferred autologous CD19-targeted T cells in patients with relapsed or chemotherapy refractory B-cell leukemias, Blood, 118(18), 4817-4828, 2011.

Brentjens, et al., Treatment of Chronic Lymphocytic Leukemia With Genetically Targeted Autologous T Cells: Case Report of an Unforeseen Adverse Event in a Phase I Clinical Trial, The American Society of Gene Therapy, 18 (4), 666-668, Apr. 2010.

Breslin, Cytokine-Release Syndrome: Overview and Nursing Implications, Clinical Journal of Oncology Nursing, 11 (1), 37-42, Jan. 24, 2007.

Caimi, et al., 738 CAR-T Therapy for Lymphoma with Prophylactic Tocilizumab: Decreased Rates of Severe Cytokine Release Syndrome without Excessive Neurologic Toxicity, 62nd ASH Annual Meeting and Exposition, Abstract 738, 1-3, Dec. 2020.

Cartellieri, et al., Chimeric Antigen Receptor-Engineered T Cells for Immunotherapy of Cancer, Journal of Biomedicine and Biotechnology, 2010, Article ID 956304, 2010.

Cavaillon, et al., The Pro-Inflammatory Cytokine Cascade, Immune Response in the Critically III. Update in Intensive Care Medicine, 2002.

Centre Daily Times newspaper published May 31, 2012, front page, pp. A7 and A9.

Charles, et al., Regulation of Cytokines, Cytokine Inhibitors, and Acute-Phase Proteins Following Anti-TNF-a Therapy in Rheumatoid Arthritis, Journal of Immunology, 163(3), 1521-1528, Aug. 1, 1999.

Chinnasamy, et al., Local Delivery of Interleukin-12 Using T Cells Targeting VEGF Receptor-2 Eradicates Multiple Vascularized Tumors in Mice, Clinical Cancer Research, 18(6), 1672-1683, Mar. 15, 2012.

Choy, et al., Translating IL-6 biology into effective treatments, Nature Reviews Rheumatology, 16, 335-345, Jun. 2020.

Claims submitted to Examining Division, Jan. 18, 2022, in European Patent Application No. 21215762.2.

Clinical trial NCT01029366, Jun. 7, 2012, available at https://www.clinicaltrials.gov/study/NCT01029366? tab=history&a=5.

Clinical trial NCT01626495 Study Protocol and Statistical Analysis Plan, Dec. 15, 2015.

Clinical trial NCT01626495, Jun. 21, 2012, available at https://clinicaltrials.gov/study/NCT01626495?tab=history&a=1.

Cohen, et al., A randomized, double-blind study of AMG 108 (a fully human monoclonal antibody to IL-1R1) in patients with osteoarthritis of the knee, Arthritis Research & Therapy, 13, R125, 2011.

Collins, et al., Donor Leukocyte Infusions in 140 Patients With Relapsed Malignancy After Allogeneic Bone Marrow Transplantation, Journal of Clinical Oncology, 15(2), 433-444, Feb. 1997.

Collins, et al., Donor leukocyte infusions in acute lymphocytic leukemia, Bone Marrow Transplantation, 26, 511-516, 2000.

Common Terminology Criteria for Adverse Events, CTCAE, 2010, pp. 1-196.

Cordeiro, et al., Late Effects of CD19-Targeted CAR-T Cell Therapy, Blood, 132(suppl. 1), 223, Nov. 29, 2018.

Costa, et al., Anakinra (AKR) prophylaxis (ppx) in patients (pts) with relapsed/refractory multiple myeloma (RRMM) receiving orvacabtagene autoleucel ( orva-cel), Journal of Clinical Oncology, 39 (suppl. 15), 2537, May 20, 2021.

Coyle, Actemra® (tocilizumab), Clinical Review, Apr. 16, 2011.

Curran, et al., Chimeric antigen receptors for T cell immunotherapy: current understanding and future directions, J Gene Med, 14, 405-415, 2012.

Cytokine Storm, Wikipedia, version of Jun. 16, 2012.

(56) References Cited

OTHER PUBLICATIONS

Davila, et al., CD19 CAR-Targeted T Cells Induce Long-Term Remission and B Cell Aplasia in an Immunocompetent Mouse Model of B Cell Acute Lymphoblastic Leukemia, PLoS ONE, 8(4), e61338, Apr. 9, 2013.
De Jong, et al., Corticosteroids inhibit the production of inflammatory mediators in immature monocyte-derived DC and induce the development of tolerogenic DC3, Journal of Leukocyte Biology, 66, 201-204, Aug. 1999.
De Kruif, et al., Prednisolone Dose-Dependently Influences Inflammation and Coagulation during Human Endotoxemia, Journal of Immunology, 178(3), 1845-1851, Feb. 1, 2007.
Decision to maintain European patent EP2872171 in amended form, Jun. 26, 2023, 24 pages.
Decision to revoke European patent EP3338794, Feb. 10, 2023, 11 pages.
Declaration of Dr Carl H. June, May 28, 2022, filed in Opposition proceedings for EP2872171.
Declaration of Dr John Maher, 2023, pp. 1-7, filed in Opposition proceedings for EP4019041.
Declaration of Dr Stephan Grupp, dated Mar. 7, 2024, filed in Opposition proceedings for EP2872171.
Declaration of Dr. Parameswaran Hari, Nov. 23, 2020, filed in opposition proceedings for EP3338794.
Declaration of Prof. Dr. Med. Olaf Penack, Dec. 14, 2022, filed in opposition proceedings for EP2872171.
Declaration of Prof. Robert Negrin, Feb. 22, 2023, filed in opposition proceedings for EP2872171.
Definition of 'following' in the Cambridge dictionary.
Definition of 'following' in the Collins Dictionary.
Definition of 'following' in the Merriam-Webster dictionary.
Definition of 'following' in the Oxford Advanced Learner's Dictionary, www.oxfordlearnersdictionaries.com/definition/english/following_3.
Definition of 'following' in the Vocabulary Dictionary.
Dhimolea, Canakinumab, mAbs, 2(1), 3-13, Jan./Feb. 2010.
Dominguez, et al., Metabolic and vascular effects of tumor necrosis factor-alpha blockade with etanercept in obese patients with type 2 diabetes, Journal of Vascular Research, 42, 517-525, 2005.
Dotti, et al., Fifteen Years of Gene Therapy Based on Chimeric Antigen Receptors: "Are We Nearly There Yet?", Human Gene Therapy, 20, 1229-1239, Nov. 2009.
Drobyski, et al., Tocilizumab for the Treatment of Steroid Refractory Graft-versus-Host Disease, Biology of Blood and Marrow Transplantation, 17, 1855-1877, 2011.
Du Bois, et al., Randomized placebo-controlled clinical trial of high-dose interleukin-2 in combination with a soluble p75 tumor necrosis factor receptor immunoglobulin G chimera in patients with advanced melanoma and renal cell carcinoma, Journal of Clinical Oncology, 15(3), 1052-1062, Mar. 1997.
EMA Assessment Report for RoActemra (tocilizumab), EMEA/26276/2009, pp. 1-55, URL: https://www. • ma.europa.eu/en/documents/assessment-report/roactemra-epar-public-assessment-report_en.pdf.
Emily Whitehead's Story: CART Cell Therapy for Acute Lymphoblastic Leukemia; available at https://www.chop.edu/video/emily-whiteheads-story-t-cell-therapy-acute-lymphoblastic-leukemia; accessed 2023.
Eshhar, et al., Specific activation and targeting of cytotoxic lymphocytes through chimeric single chains consisting of antibody-binding domains and the gamma or zeta subunits of the immunoglobulin and T-cell receptors, Proc. Natl. Acad. Sci. USA, 90, 720-724, Jan. 1993.
Evidence showing that Drobyski, et al. was published online on Jul. 11, 2011.
Excerpt from book 'Praying for Emily' by Tom, Kari and Emily Whitehead, 2020, pp. 187-194.
Ferrara, et al., Graft-versus-host disease, Lancet, 373, 1550-1561, Mar. 12, 2009.
Figure 8 v Figure 9 of U.S. Appl. No. 61/671,482, filed in opposition proceedings for EP2872171.
Fuerst, Genetically Engineered T-cell Therapy Induces Durable Responses in Refractory Leukemias, Oncology Times, 35(4), 20-21, Feb. 25, 2013.
Garcia-Manero, et al., Salvage Therapy for Refractory or Relapsed Acute Lymphocytic Leukemia, Hematology/Oncology Clinics of North America, 15(1), 163-205, Feb. 2001.
Gazeau, et al., Safety and Efficacy of Two Anakinra Dose Regimens for Refractory CRS or leans after CAR T-Cell Therapy, Blood, 138(suppl. 1), 2816, Nov. 5, 2021.
Goffe, et al., Etanercept: An overview, Journal of the American Academy of Dermatology, 49(2), 105-111, 2003.
Gokbuget, et al., Outcome of relapsed adult lymphoblastic leukemia depends on response to salvage chemotherapy, prognostic factors, and performance of stem cell transplantation, Blood, 120(10), 2032-2041, Sep. 6, 2012.
Goujon, et al., A new bioinformatics analysis tools framework at EMBL-EBI, Nucleic Acids Research, 38, W695-W699, May 3, 2010.
Grady, In Girl's Last Hope, Altered Immune Cells Beat Leukemia, The New York Times, Dec. 9, 2012.
Grupp, CD19 Lentiviral T body Protocol, Version 15.12-15-2015, 83 pages.
Grupp, et al., CD19-Redirected Chimeric Antigen Receptor T (CART19) Cells Induce a Cytokine Release Syndrome (CRS) and Induction of Treatable Macrophage Activation Syndrome (MAS) That Can Be Managed by the IL-6 Antagonist Tocilizumab (toc), Blood, 120(21), abstract 2604, Nov. 16, 2012.
Grupp, et al., Chimeric Antigen Receptor—Modified T Cells for Acute Lymphoid Leukemia, The New England Journal of Medicine, 368(16), 1509-1518, Apr. 18, 2013.
Grupp, et al., Chimeric Antigen Receptor-Modified T Cells for Acute Lymphoid Leukemia, The New England Journal of Medicine (Supplementary materials), 368(16), 1509-1518, Apr. 18, 2013.
Gust, et al., Endothelial activation and blood-brain barrier disruption in neurotoxicity after adoptive immunotherapy with CD19 CAR-T cells, Cancer Discovery, 7(12), 1404-1419, Dec. 2017.
Hansel, et al., The safety and side effects of monoclonal antibodies, Nature Reviews Drug Discov., 9, 325-338, Apr. 2010.
Henderson, et al., Comparison of the effects of FK-506, cyclosporin A and rapamycin on IL-2 production, Immunology, 73, 316-321, 1991.
Hennigan, et al., Interleukin-6 inhibitors in the treatment of rheumatoid arthritis, Ther Clin Risk Manag, 4(4), 767-775, 2008.
History of Changes for Study NCT01626495, submitted Jun. 21, 2012.
Hotfilder, et al., Leukemic Stem Cells in Childhood High-Risk ALL/t(9;22) and t(4;11) Are Present in Primitive Lymphoid-Restricted CD34+CD19- Cells, Cancer Research, 65(4), 1442-1449, Feb. 15, 2005.
Howard, et al., The Tumor Lysis Syndrome, The New England Journal of Medicine, 364(19), 1844-1854, May 12, 2011.
Huse, et al., Generation of a Large Combinatorial Library of the Immunoglobulin Repertoire in Phage Lambda, Science, 246, 1275-1281, Dec. 8, 1989.
Huston, et al., Protein engineering of antibody binding sited: recovery of specific activity in an anti-digoxin single-chain Fv analogue produced in *Escherichia coli*, Proc. Natl. Acad. Sci. USA, 85, 5879-5883, Aug. 1988.
ICMJE Form for Disclosure of Potential Conflicts of Interest, 65 pages.
Imai, et al., Chimeric receptors with 4-1BB signaling capacity provoke potent cytotoxicity against acute lymphoblastic leukemia, Leukemia, 18, 676-684, Feb. 12, 2004.
Interview with Carl June on the Onclive website, Nov. 21, 2015, https://www.onclive.com/view/june-provides-insight-into-managing-aes-from-car-t-cell-therapies.
Ishii, et al., Tocilizumab-Refractory Cytokine Release Syndrome (CRS) Triggered By Chimeric Antigen Receptor (CAR)-Transduced T Cells May Have Distinct Cytokine Profiles Compared to Typical CRS, Blood, 128 (22), 3358, 2016.
Janeway, et al., T cell-mediated cytotoxicity, Immunobiology: The Immune System in Health and Disease, 2001.

(56) References Cited

OTHER PUBLICATIONS

Janka, Familial and Acquired Hemophagocytic Lymphohistiocytosis, Annual Review of Medicine, 63, 233-246, 2012.
Jena, et al., Redirecting T-cell specificity by introducing a tumor-specific chimeric antigen receptor, Blood, 116(7), 1035-1044, Aug. 19, 2010.
Jensen, et al., Anti-Transgene Rejection Responses Contribute to Attenuated Persistence of Adoptively Transferred CD20/CD19-Specific Chimeric Antigen Receptor Re-directed T Cells in Humans, Biology of Blood and Marrow Transplantation, 16(9), 1245-1256, Sep. 2010.
Jones, et al., Therapeutic strategies for the clinical blockade of IL-6/gp130 signaling, Journal of Clinical Investigation, 121(9), 3375-3383, Sep. 2011.
Kalos, Biomarkers in T cell therapy clinical trials, Journal af Translational Medicine, 9:138, 2011.
Kalos, et al., Sustained Functional T Cell Persistence and B Cell Aplasia Following CD19-Targeting Adoptive T Cell Immunotherapy for Relapsed, Refractory CD19+ Malignacy, Blood, 120(21), abstract 756, Nov. 16, 2012.
Kalos, et al., T Cells with Chimeric Antigen Receptors Have Potent Antitumor Effects and Can Establish Memory in Patients with Advanced Leukemia, Science Translation Medicine, 3(95), 95ra73, 1-11, Aug. 10, 2011.
Kalos, et al., T Cells with Chimeric Antigen Receptors Have Potent Antitumor Effects and Can Establish Memory in Patients with Advanced Leukemia, Science Translation Medicine, 3, 95ra73, Aug. 10, 2011.
Kamarasheva, et al., Generalised Pustular Psoriasis Induced by Cyclosporin A Withdrawal Responding to the Tumour Necrosis Factor Alpha Inhibitor Etanercept, Dermatology, 205, 213-216, 2002.
Kanellis, et al., Uric Acid Stimulates Monocyte Chemoattractant Protein -! Production in Vascular Smooth Muscle Cells Via Mitogen-Activated Protein Kinase and Cyclooxygenase-2, Hypertension, 41, 1287-1293, Jun. 2003.
Kang, et al., shRNA-Interleukin-6 Modified CD19-Specific Chimeric Antigen Receptor T Cell Significantly Improves the Safety in Acute Lymphoblastic Leukemia, Blood, 134(Suppl. 1), Abstract 2621, Nov. 13, 2019.
Kaplanski, et al., IL-6: a regulator of the transition from neutrophil to monocyte recruitment during inflammation, Trends in Immunology, 24(1), 25-29, Jan. 2003.
Kishimoto, Interleukin-6: discovery of a pleiotropic cytokine, Arthritis Research and Therapy, 8(suppl. 2), Jul. 28, 2006.
Kochenderfer, et al., B-cell depletion and remissions of malignancy along with cytokine-associated toxicity in a clinical trial of anti-CD19 chimeric-antigen-receptor-transduced T cells, Blood, 119(12), 2709-2720, Mar. 22, 2012.
Kochenderfer, et al., Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor, Journal of Clinical Oncology, 33(6), 540-549, Feb. 20, 2015.
Kochenderfer, et al., Construction and Pre-clinical Evaluation of an Anti-CD19 Chimeric Antigen Receptor, Journal of Immunotherapy, 32(7), 689-702, Sep. 2009.
Kochenderfer, et al., Eradication of B-lineage cells and regression of lymphoma in a patient treated with autologus T cells genetically engineered to recognize CD19, Blood, 116(20), 4099-4102, Nov. 18, 2010.
Kohler, et al., Continuous cultures of fused cells secreting antibody of predefined specificity, Nature, 256, 495-497, Aug. 7, 1975.
Kolb, et al., Graft-Versus-Leukemia Effect of Donor Lymphocyte Transfusions in Marrow Grafted Patients, Blood, 86(5), 2041-2050, Sep. 1, 1995.
Kruttgen, et al., Interleukin-6 in Sepsis and Capillary Leakage Syndrome, Journal of Interferon and Cytokine Research, 32(2), 60-65, 2012.
Land, Future Immunosuppression in Organ Transplantation: Treating the Innate Immune System of the Deceased Donor-Start Tomorrow, Experimental and Clinical Transplantation, 3, 195-208, 2012.
Larimore, et al., Shaping of Human Germline IgH Repertoires Revealed by Deep Sequencing, Journal of Immunology, 189(6), 3221-3230, Sep. 15, 2012.
Le Huu, et al., IL-6 Blockade Attenuates the Development of Murine Sclerodermatous Chronic Graft-Versus-Host Disease, Journal of Investigative Dermatology, 132, 2752-2761, 2012.
Le Viseur, et al., In Childhood Acute Lymphoblastic Leukemia, Blasts at Different Stages of Immunophenotypic Maturation Have Stem Cell Properties, Cancer Cell, 14, 47-58, Jul. 2008.
Lee, et al., Current concepts in the diagnosis and management of cytokine release syndrome, Blood, 124(2), 188-195, Jul. 10, 2014.
Lee, et al., Monoclonal antibodies and fusion proteins and their complications: Targeting B cells in autoimmune diseases, Journal of Allergy and Clinical Immunology, 125(4), 814-820, 2010.
Leung, et al., Update on glucocorticoid action and resistance, Journal of Allergy and Clinical Immunology, 111(1), 3-22, 2003.
Lipowska-Bhalla, et al., Targeted immunotherapy of cancer with CAR T cells: achievements and challenges, Cancer Immunol Immunother, 61, 953-962, 2012.
Liu, et al., Calcineurin Is a Common Target of Cyclophilin-Cyclosporin A and FKBP-FK506 Complexes, Cell, 66, 807-815, Aug. 23, 1991.
Losa Garcia, et al., Cyclosporin A decreases human macrophage interleukin-6 synthesis at post-transcriptional level, Mediators of Inflammation, 8, 253-259, 1999.
Madhusudan, et al., A Phase II Study of Etanercept (Enbrel), a Tumor Necrosis Factor a Inhibitor in Patients with Metastatic Breast Cancer, Clinical Cancer Research, 10, 6528-6534, Oct. 1, 2004.
Majzner, et al., Abstract CT031: 0D2 CAR T cells mediate clinical activity and manageable toxicity in children and young adults with DIPG and H3K27M-mutated diffuse midline gliomas, Cancer Res, 81(Suppl._13), CT031, 2021.
Martn, et al., First- and Second-Line Systemic Treatment of Acute Graft-versus-Host Disease: Recommendations of the American Society of Blood and Marrow Transplantation, Biology of Blood and Marrow Transplantation, 18, 1150-1163, 2012.
Meier, et al., Current immunotherapy in rheumatoid arthritis, Immunotherapy, 5(9), 955-974, 2013.
Mihara, et al., The therapy of autoimmune diseases by anti-interleukin-6 receptor antibody, Expert Opin. Biol Ther., 5(5), 683-690, 2005.
Milone, et al., Chimeric Receptors Containing CD137 Signal Transduction Domains Mediate Enhanced Survival of T Cells and Increased Antileukemic Efficacy In Vivo, Molecular Therapy, 17(8), 1453-1464, Aug. 2009.
Molostova, et al., Local Manufacture of CD19 CAR-T Cells Using an Automated Closed-System: Robust Manufacturing and High Clinical Efficacy with Low Toxicities, Blood, 134(Suppl. 1), Abstract 2625, 2019.
Morgan, et al., Case Report of a Serious Adverse Event Following the Administration of T Cells Transduced With a Chimeric Antigen Receptor Recognizing ERBB2, Molecular Therapy, 18(4), 843-851, Apr. 2010.
Myers, et al., Risk-Adapted Preemptive Tocilizumab Decreases Severe Cytokine Release Syndrome (CRS) after CTL019 CD19-Targeted Chimeric Antigen Receptor ( CAR) T-Cell Therapy for Pediatric B-Cell Acute Lymphoblastic Leukemia (B-ALL), Biol Blood Marrow Transpl., 26 (49), S39, 2020.
Navai, et al., Abstract LB-147: Administration of HER2-CAR T cells after lymphodepletion safely improves T cell expansion and induces clinical responses in patients with advanced sarcomas, Cancer Research, 79(Suppl._13), 1-2, 2019.
Nellan, et al., Improved CNS exposure to tocilizumab after cerebrospinal fluid compared to intravenous administration in rhesus macaques, Blood, 132(6), 662-666, Aug. 9, 2018.
Nestorov, et al., Pharmacokinetics of subcutaneously administered etanercept in subjects with psoriasis, British Journal of Clinical Pharmacology, 62(4), 435-445, Feb. 14, 2006.
New England Journal of Medicine Issue Index for articles published in Aug. 2011.

(56) References Cited

OTHER PUBLICATIONS

News release by the American Association for Cancer Research, Steven A. Rosenberg, MD, PhD, FAACR, recognized with 2022 Pezcoller Foundatio•• AACR International Award for Extraordinary Achievement in Cancer Research, Mar. 23, 2022.
Nishimoto, et al., Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease, Blood, 112(10), 3959-3964, Nov. 15, 2008.
Noguchi, et al., Blockade of IL-6-signaling inhibits the pathogenesis of CD4+ T cell-mediated lethal graft-versus-host reaction against minor histocompatibility antigen, Immunology Letters, 136, 146-155, Jan. 20, 2011.
Observations filed by Patentees in opposition proceedings of EP3338794.
Ogata, et al., Tocilizumab for the Treatment of Rheumatoid Arthritis and Other Systemic Autoimmune Diseases: Current Perspectives and Future Directions, International Journal of Rheumatology, 2012, article ID 946048, 2012.
Okuda, Review of tocilizumab in the treatment of rheumatoid arthritis, Biologics: Targets & Therapy, 2(1), 75-82, 2008.
Olson, et al., Shipping blood to a central laboratory in multicenter clinical trials: effect of ambient temperature on specimen temperature, and effects of temperature on mononuclear cell yield, viability and immunologic function, Journal of Translational Medicine, 9:26, 2011.
Overview of Abecma (idecabtagene vicleucel) , EMA.
Overview of Breyanzi (lisocabtagene maraleucel), EMA.
Overview of Kymriah (tisagenlecleucel), European Medicines Agency.
Overview of Tecartus (autologous anti-CD19-transduced CD3+ cell), EMA.
Overview of Yescarta (axica btagene ciloleucel) , EMA.
Owyang, et al., XOMA 052, a potent, high-affinity monoclonal antibody for the treatment of IL-1beta-mediated diseases, mAbs, 3(1), 49-60, Jan./Feb. 2011.
Patentees' letter to Examining Division, Jan. 18, 2022, in European Patent Application No. 21215762.2.
Patentees' letter to Examining Division, Jul. 22, 2022, in European Patent Application No. 21215762.2.
Patentees' reply to the opposition in EP2872171.
Pilat, et al., Costimulatory pathways in transplantation, Seminars in Immunology, 23, 293-303, 2011.
Ponce, Adverse Consequences of Immunostimulation, Journal of Immunotoxicology, 5(1), 33-41, Oct. 9, 2008.
Porter, et al., Chimeric Antigen Receptor—Modified T Cells in Chronic Lymphoid Leukemia, The New England Journal of Medicine, 365(8), 725-733, Aug. 25, 2011.
Porter, et al., Chimeric Antigen Receptor T Cells Directed Against CD19 Induce Durable Responses and Transient Cytokine Release Syndrome in Relapsed, Refractory CLL and ALL, Blood, 120(21), abstract 717, Nov. 16, 2012.
Porter, et al., Chimeric Antigen Receptor Therapy for B-cell Malignancies, Journal of Cancer, 2, 331-332, 2011.
Prieto-Moure, et al., Allopurinol Protective Effect of Renal Ischemia by Down regulating TNF-a, IL-1 p, and IL-6 Response, Journal of Investigative Surgery,, 30, 143-151, 2017.
Pullen, et al., Extended Triple Intrathecal Chemotherapy Trial for Prevention of CNS Relapse in Good-Risk and Poor-Risk Patients With B-Progenitor Acute Lymphoblastic Leukemia: A Pediatric Oncology Group Study, Journal of Clinical Oncology, 11(5), 839-849, May 1993.
Queen, et al., A humanized antibody that binds to the interleukin 2 receptor, Proc. Natl. Acad. Sci. USA, 86, 10029-10033, Dec. 1989.
Ramos, et al., Chimeric antigen receptor (CAR)-engineered lymphocytes for cancer therapy, Expert Opinion on Biological Therapy, 11(7), 855-873, Apr. 4, 2011.
Ravelli, et al., Macrophage activation syndrome as part of systemic juvenile idiopathic arthritis: diagnosis, genetics, pathophysiology and treatment, Genes and Immunity, 13, 289-298, Mar. 15, 2012.
Redlined claims submitted to Examining Division, Jul. 22, 2022, in European Patent Application No. 21215762.2.
Reiff, Treatment of Systemic Juvenile Idiopathic Arthritis with Tocilizumab—the Role of Anti-Interleukin-6 Therapy After a Decade of Treatment, Biologics in Therapy, 2, 2012.
Reply of Patent Proprietor to Notices of Opposition, EP3338794, Jun. 25, 2021.
Restifo, et al., Adoptive immunotherapy for cancer: harnessing the T cell response, Nature Reviews Immunology, 12, 269-281, Apr. 2012.
Ridker, et al., Interleukin-1β inhibition and the prevention of recurrent cardiovascular events: Rationale and Design of the Canakinumab Anti-inflammatory Thrombosis Outcomes Study (CANTOS), American Heart Journal, 162(4), 597-605, Oct. 2011.
Robins, et al., Comprehensive assessment of T-cell receptor beta-chain diversity in alphabeta T cells, Blood, 114 (19), 4099-4107, Nov. 5, 2009.
Rosenberg, et al., Use of Tumor-Infiltrating Lymphocytes and Interleukin-2 in the Immunotherapy of Patients With Metastatic Melanoma, The New England Journal of Medicine, 319, 1676-1680, Dec. 22, 1988.
Said, et al., Defining I L-6 levels in healthy individuals: A meta-analysis, Journal of Medical Virology, 93, 3915-3924, 2021.
Sandilands, et al., Were monocytes responsible for initiating the cytokine storm in the TGN1412 clinical trial tragedy?, Clinical and Experimental Immunology, 162, 516-527, 2010.
Savoldo, et al., CD28 costimulation improves expansion and persistence of chimeric antigen receptor-modified T cells in lymphoma patients, The Journal of Clinical Investigation, 121(5), 1822-1826, May 2011.
Science Daily, Leukemia patients remain in remission more than two years after engineered T cell therapy, Dec. 10, 2012.
Screenshots and transcript of Dr. Carl June YouTube recording, Celebration of Science, Nov. 6, 2012, Prostate Cencer Foundation. Available online at https://www.youtube.com/watch?v=jQ4pFMpAdO0&t=934s.
Second Declaration of Dr. John Maher, 2025, filed in Opposition proceedings for EP4019041.
Second declaration of Prof. Robert Negrin, Feb. 22, 2023, filed in opposition proceedings for EP2872171.
Second Declaration Prof. Dr. Med. Olaf Penack, Sep. 21, 2023, filed in opposition proceedings for EP2872171.
Sha, et al., Effect of Etanercept (Enbrel) on Interleukin 6, Tumor Necrosis Factor a, and Markers of Immune Activation in HIV-Infected Subjects Receiving Interleukin 2, AIDS Research and Human Retroviruses, 18(9), 661-665, 2002.
Shah, et al., High Rates of Minimal Residual Disease-Negative (MRD-) Complete Responses (CR) in Adult and Pediatric and Patients With Relapsed/Refractory Acute Lymphoblastic Leukemia (R/R ALL), Blood, 128(22), Abstract 2803, Dec. 2, 2016.
Shah, et al., Minimal Residual Disease Negative Complete Remissions Following Anti-CD22 Chimeric Antigen Receptor (CAR) in Children and Young Adults with Relapsed/Refractory Acute Lymphoblastic Leukemia (ALL), Blood, 128(22), 650, Dec. 2, 2016.
Shen, et al., Etanercept Restores the Antinociceptive Effect of Morphine and Suppresses Spinal Neuroinflammation in Morphine-Tolerant Rats, Anesthesia & Analgesia, 112(2), 454-459, Feb. 2011.
Sievers, et al., Fast, scalable generation of high-quality protein multiple sequence alignments using Clustal Omega, c, 7, article No. 539, 2011.
Siltuximab Inn, WHO Drug Information, 2008, 22(4), pp. 311-312 and 340-341.
Sims, et al., The IL-1 family: regulators of immunity, Nature Reviews Immunology, 10, 89-102, Feb. 2010.
Stambrook, et al., Cancer Immunotherapy: Whence and Whither, Mol. Cancer Res., 15(6), 635-650, Jun. 2017.
Sullivan, et al., Measurement of Cytokine Secretion, Intracellular Protein Expression, and mRNA in Resting and Stimulated Peripheral Blood Mononuclear Cells, Clinical Diagnostic Laboratory Immunology, 7(6), 920-924, Nov. 2000.

(56) References Cited

OTHER PUBLICATIONS

Summary of Product Characteristics (Annex I) for Kymriah, an antiCD19 CAR Tcell therapy, available at https://www.ema.europa.eu/en/documents/productinformation/kymriah-epar-product-information_en.pdf.
Suntharalingam, et al., Cytokine Storm in a Phase 1 Trial of the Anti-CD28 Monoclonal Antibody TGN1412, The New England Journal of Medicine, 355(10), 1018-1028, Sep. 7, 2006.
Szyper-Kravitz, The Hemophagocytic Syndrome/Macrophage Activation Syndrome: A Final Common Pathway of a Cytokine Storm, Israel Medical Association Journal, 11, 633-634, Oct. 2009.
Tanaka, et al., Anti-interleukin-6 receptor antibody, tocilizumab, for the treatment of autoimmune diseases, FEBS Letters, 585, 3699-3709, Mar. 16, 2011.
Tang, et al., Early diagnostic and prognostic significance of a specific Th1/Th2 cytokine pattern in children with haemophagocytic syndrome, British Journal of Haematology, 143, 84-91, Jul. 31, 2008.
Tanyi, et al., Possible Compartmental Cytokine Release Syndrome in a Patient With Recurrent Ovarian Cancer After Treatment With Mesothelin-targeted CAR-T Cells, J Immunother., 40(3), 104-107, Apr. 2017.
Tawara, et al., Interleukin-6 Modulates Graft-versus-Host Responses after Experimental Allogeneic Bone Marrow Transplantation, Clinical Cancer Research, 17(1), 77-88, 2010.
Teachey, et al., Cytokine release syndrome after blinatumomab treatment related to abnormal macrophage activation and ameliorated with cytokine-directed therapy, Blood, 121(26), 5154-5157, Jun. 27, 2013.
Temsirolimus, Wikipedia, Feb. 18, 2009.
Till, et al., Adoptive immunotherapy for indolent non-Hodgkin lymphoma and mantle cell lymphoma using genetically modified autologous CD20-specific T cells, Blood, 112(6), 2261-2271, Sep. 15, 2008.
Till, et al., CD20-specific adoptive immunotherapy for lymphoma using a chimeric antigen receptor with both CD28 and 4-1BB domains: pilot clinical trial results, Blood, 119(17), 3940-3950, Apr. 26, 2012.
Tisoncik, et al., Into the Eye of the Cytokine Storm, Microbiology and Molecular Biology Reviews, 76(1), 16-32, Mar. 2012.
Union Register of medicinal products—Public health—European Commission, RoActemra (tocilizumab).
U.S. Appl. No. 61/671,482.
U.S. Appl. No. 61/782,982.
Vadhan-Raj, et al., Randomized Clinical Trial of Rasburicase Administered as a Standard Fixed Five Days Dosing Vs a Single Dose Followed by as Needed Dosing in Adult Patients with Hematologic Malignancies at Risk for Developing Tumor Lysis Syndrome, Blood, 114 (22), abstract 105, Nov. 20, 2009.
Transcript and screenshots of YouTube recording of Dr. Carl June presentation entitled "Gene and Cell-Based Immunotherapy for Cancer", Jun. 20, 2012, video available online at: https://www.youtube.com/watch?v=VKXk6iqqMt8.
Ward, et al., Binding activities of a repertoire of single immunoglobulin variable domains secreted from *Escherichia coli*, Nature, 341, 544-546, Oct. 12, 1989.
Wei, et al., The model of cytokine release syndrome in CAR T-cell treatment for B-cell non-Hodgkin lymphoma, Signal Transduction and Targeted Therapy, 5:134, 2020.
Whiteside, Cytokines and Cytokine Measurements in a Clinical Laboratory, Clinical and Diagnostic Laboratory Immunology, 1(3), 257-260, May 1994.
Winkler, et al., Cytokine-Release Syndrome in Patients With B-Cell Chronic Lymphocytic Leukemia and High Lymphocyte Counts After Treatment With an Anti-CD20 Monoclonal Antibody, Blood, 94 (7), 2217-2224, Oct. 1, 1999, WO.
Wong, et al., Anakinra Targeting Cytokine Release Syndrome Associated with Chimeric Antigen Receptor T-Cell Therapies, Blood, 138(suppl. 1), 2812, Nov. 5, 2021.
Yanez, et al., CAR T Cell Toxicity: Current management and Future Directions, HemaSphere, 3(2), e186, 2019.
Yanik, et al., The impact of soluble tumor necrosis factor receptor etanercept on the treatment of idiopathic pneumonia syndrome after allogeneic hematopoietic stem cell transplantation, Blood, 112(8), 3073-3081, Oct. 15, 2008.
Yiu, et al., Dynamics of a Cytokine Storm, Plos One, 7(10), e45027, Oct. 1, 2012.
Supplementary Materials for Kalos et al. (2011) T Cells with Chimeric Antigen Receptors Have Potent Antitumor Effects and Can Establish Memory in Patients with Advanced Leukemia, Science Translational Medicine 3(95):95ra73 (25 pages).
Boult Wade Tennant LLP, "Notice of Opposition to a European Patent and Opposition to EP3338794" dated Nov. 13, 2020, 54 pages.
Maiwald Patentanwalts- und Rechtsanwaltsgesellschaft mbH on behalf of Gedeon Richter Pharma GmbH, "Notice of Opposition to a European Patent and Opposition to EP3338794" dated Nov. 25, 2020, 39 pages.
Hoffmann Eitle Patent- und Rechtsanwalte Partnerschaftsgesellschaft mbB, "Notice of Opposition to a European Patent and Opposition to EP3338794" dated Nov. 25, 2020, 79 pages.
Strawman Limited, "Notice of Opposition to a European Patent and Opposition to EP3338794" dated Nov. 26, 2020, 66 pages.
Secerna LLP, "Opposition to EP3338794" dated Nov. 26, 2020, 42 pages.
Gerhard Weinzierl, "Notice of Opposition to a European Patent and Opposition to EP3338794" dated Nov. 26, 2020, 32 pages.
ZSP Patentanwalte PartG mbB, "Notice of Opposition to a European Patent and Opposition to EP3338794" dated Nov. 26, 2020, 55 pages.
Strawman Limited, "Opposition to EP2872171" dated Oct. 6, 2021, 91 pages.
Boult Wade Tennant LLP, "Notice of Opposition to a European Patent and Opposition to EP2872171" dated Sep. 24, 2021, and Oct. 6, 2021, 76 pages.
Secerna LLP, "Notice of Opposition to a European Patent and Opposition to EP2872171" dated Oct. 5, 2021, 47 pages.
Maiwald Patentanwalts- und Rechtsanwaltsgesellschaft mbH on behalf of Gedeon Richter Pharma GmbH, Opposition to EP2872171 dated Oct. 6, 2021, 44 pages.
D Young & Co, Third Party Observations Against European Patent No. 2872171, Sep. 13, 2018, 12 pages.
Patentees' Submission in Opposition to European Patent No. 2872171, Feb. 24, 2023, 94 pages.
Maiwald GmbH, Further Submission in Opposition to European Patent No. 2872171, Dec. 15, 2022, 13 pages.
Secerna LLP, Withdrawal of Opposition to European Patent No. 2872171, Nov. 7, 2023, 1 page.
Boult Wade Tennant LLP, Request for Correction of Minutes in Oppostion to European Patent No. 2872171, Nov. 6, 2023, 1 page.
Boult Wade Tennant LLP, Further Submission in Opposition to European Patent No. 2872171, Feb. 24, 2023, 39 pages.
Boult Wade Tennant LLP, Further Submission in Opposition to European Patent No. 2872171 with D100, Apr. 19, 2023, 3 pages.
Strawman Limited, Grounds of Appeal in Opposition to European Patent No. 2872171, Nov. 6, 2023, 40 pages.
Boult Wade Tennant LLP, Grounds of Appeal in Opposition to European Patent No. 2872171, Nov. 6, 2023, 91 pages.
Maiwald GmbH, Grounds of Appeal in Opposition to European Patent No. 2872171, Nov. 6, 2023, 34 pages.
Boult Wade Tennant LLP, Further Submission in Opposition to European Patent No. 2872171, Oct. 20, 2024, 28 pages.
Maiwald GmbH, Further Submission in Opposition to European Patent No. 2872171, Feb. 5, 2025, 18 pages.
Maiwald GmbH, Further Submission in Opposition to European Patent No. 2872171, Sep. 24, 2025, 23 pages.
Patentees' Reply to Appeals in Opposition to European Patent No. 2872171, Mar. 11, 2024, 184 pages.
Patentees' Letter to the Board in Opposition to European Patent No. 2872171, Jun. 30, 2025, 5 pages.
Preliminary Opinion of the Board of Appeal in Opposition to European Patent No. 2872171, Jul. 2, 2025, 18 pages.

(56) References Cited

OTHER PUBLICATIONS

Board of Appeals Decision to Dismiss the Appeals in Opposition to European Patent No. 2872171, Feb. 13, 2026, 61 pages.
Boult Wade Tennant LLP—Third Party Observations dated Aug. 7, 2024, in European Patent Application No. 20158930.6, 4 pages.
Schiweck Weinzierl Koch Patentanwälte Partnerschaft mbB—Third Party Observations against European Patent No. 4019041 dated Dec. 19, 2022, 10 pages.
Boult Wade Tennant LLP, Opposition to European Patent No. 4019041, Sep. 28, 2023, 68 pages.
Maiwald GmbH, Opposition to European Patent No. 4019041, Sep. 28, 2023, 38 pages.
Patent Boutique LLP, Opposition to European Patent No. 4019041, Sep. 28, 2023, 54 pages.
Boult Wade Tennant LLP, Further Submission in Opposition to European Patent No. 4019041, Nov. 27, 2023, 22 pages.
Boult Wade Tennant LLP, Further Submission in Opposition to European Patent No. 4019041, Sep. 12, 2025, 52 pages.
Maiwald GmbH, Further Submission in Opposition to European Patent No. 4019041, Aug. 1, 2024, 9 pages.
Maiwald GmbH, Further Submission in Opposition to European Patent No. 4019041, Jul. 31, 2025, 16 pages.
Patent Boutique LLP, Further Submission in Opposition to European Patent No. 4019041, Sep. 12, 2025, 20 pages.
Patentees' Reply to Oppositions to European Patent No. 4019041, May 21, 2024, 431 pages.
Patentees' Further Reply to Oppositions to European Patent No. 4019041, Sep. 12, 2025, 4 pages.
Patentees' Further Reply to Oppositions to European Patent No. 4019041, Oct. 31, 2025, 4 pages.
Opposition Division, Preliminary Opinion and Summons to Oral Proceedings in Oppositions to European Patent No. 4019041, Aug. 5, 2024, 61 pages.
Opposition Division, Preliminary Opinion and Summons to Oral Proceedings in Oppositions to European Patent No. 4019041, Oct. 24, 2024, 61 pages.
Screenshot of Leucid Bio webpage, www.leucid.com/industries, accessed Sep. 25, 2025, 1 page.
Van Schalwyk, et al., "Design of a Phase I Clinical Trial to Evaluate Intratumoral Delivery of ErbB-Targeted Chimeric Antigen Receptor T-Cells in Locally Advanced or Recurrent Head and Neck Cancer" Hum Gene Ther Clin Dev. (2013);24:134-142.
Boult Wade Tennant LLP, Opposition to European Patent No. 4461308, Jan. 16, 2026, 84 pages.
Patent Boutique LLP, Opposition to European Patent No. 4461308, Jan. 21, 2026, 44 pages.
Morris, et al., "Cytokine release syndrome and associated neurotoxicity in cancer immunotherapy" Nature Reviews Immunology (2022) 22:85-96.
Siegler, et al., "Neurotoxicity and Cytokine Release Syndrome after Chimeric Antigen Receptor T Cell Therapy: Insights into Mechanisms and Novel Therapies; a Review"; Frontiers in Immunology, Aug. 2020, vol. 11, Article 1973.
Locke, et al., "Preliminary Results of Prophylactic Tocilizumab after Axicabtageneciloleucel ( axi-cel; KTEC 19) Treatment for Patients with Refractory, Aggressive Non-Hodgkin Lymphoma (NHL)"; Blood (2017) vol. 130 (Supplement 1) 1547, Dec. 7, 2017.
Patentees' Letter to the European Patent Officein European Patent Application No. 24202493.3, Sep. 25, 2024, 3 pages.
Chen, et al., "Blockade of Interleukin-6 signaling augments regulatory T-cell constitution and attenuates the severity of graft-versus-host disease"; Blood, 114(4) 891-900, Jul. 23, 2009.
Trikha, et al., "Targeted Anti-Interleukin-6 Monoclonal Antibody Therapy for Cancer: A Review of the Rationale and Clinical Evidence"; Clinical Cancer Res., 9:4653-4665, Oct. 15, 2023.
Tanaka, et al., "Therapeutic Targeting of the Interleukin-6 Receptor" Annu. Rev. Pharmacol. Toxicol. (2012) 52:199-219.
Malemud, "Recent advances in neutralizing the IL-6 pathway in arthritis" Open Access Rhuematology: Research and Reviews (2009) 1: 133-150.
Frigault, et al., "A Phase II Trial of Anakinra for the Prevention of CAR-T Cell Mediated Neurotoxicity", Blood (2021) 138(Supplement 1):2814.
Lie, et al., "The biology of interleukin-1: emerging concepts in the regulation of the actin cytoskeleton and cell junction dynamics", Cell Mol Life Sci. Feb. 2012; 69(4): 487-500.
Wesche, et al., "The Interleukin-1 Receptor Accessory Protein (IL-1RAcP) Is Essential for IL-1-induced Activation of Interleukin-1 Receptor-associated Kinase (IRAK) and Stress-activated Protein Kinases (SAP Kinases)", J. Biol. Chem., 1997, 272(12):7727-7731.
Garrone, et al., "Generation and characterization of a humanmonoclonal autoantibody that acts as a high affinityinterleukin-1 alpha specific inhibitor", Mol. Immunol., May-Jun. 1996; 33(7-8):649-58, Abstract.
Mansur, et al., "Engagement of IL-1 receptor accessory protein (IL-1RAcP) with the monoclonal antibody AY19 provides co-activating signals and prolongs the CD2-induced proliferation of peripheral blood lymphocytes", Immunol. Letters, Sep. 2011, 139(1-2):52-57, Abstract.
Jaras, et al., "Isolation and killing of candidate chronic myeloid leukemia stem cells by antibody targeting of IL-1 receptor accessory protein", Proc. Natl. Acad. Sci., U.S.A., Sep. 14, 2010; 107(37):16280-16285.
Boult Wade Tennant LLP, Further Submission in Opposition to European Patent No. 3338794, Oct. 5, 2022, 40 pages.
Declaration of Mark D. Simpson, Jun. 23, 2021, filed in Opposition proceedings for EP3338794.
Gerhard Weinzierl, Further Submission in Opposition Proceedings for EP3338794, Oct. 5, 2022, 9 pages.
Hoffmann Eitle Patent- und Rechtsanwalte Partnerschaftsgesellschaft mbB, Submission in Opposition Proceedings for EP3338794, Oct. 5, 2022, 7 pages.
Hoffmann Eitle Patent- und Rechtsanwalte Partnerschaftsgesellschaft mbB, Submission in Opposition Proceedings for EP3338794, Nov. 17, 2022, 15 pages.
Maiwald Patentanwalts- und Rechtsanwaltsgesellschaft mbH, Submission in Opposition Proceedings for EP3338794, Oct. 5, 2022, 10 pages.
Secerna Llp, Submission in Opposition Proceedings for EP3338794, Oct. 5, 2022, 32 pages.
Strawman Limited, Submission in Opposition Proceedings for EP3338794, Oct. 5, 2022, 36 pages.
ZSP Patentanwalte PartG mbB, Submission in Opposition Proceedings for EP3338794, Oct. 5, 2022, 13 pages.
Declaration of Bruce L. Levine, Jun. 23, 2021, filed in Opposition proceedings for EP3338794.
Chen, et al., "Section II Common Properties of Cytokines and Their Primary Biological Effects", Pathogenic Biology and Immunology, p. 38, 2011.
Corrected filing receipt issued by USPTO on Aug. 14, 2012 in U.S. Appl. No. 61/671,482.
Davila, et al., "Chimeric antigen receptors for the adoptive T cell therapy of hematologic malignancies", Int. J Hematol., vol. 99, No. 4, pp. 361-367.
Opposition Division, Outcome of Oral Proceedings re EP13817210, Apr. 27, 2023, 5 pages.
Opposition Division, Interlocutory Decision in Opposition Proceedings for EP2872171, Jun. 26, 2023, 98 pages.
Le, et al. "FDA approval summary: tocilizumab for treatment of chimeric antigen receptor T cell-induced severe or life-threatening cytokine release syndrome." The Oncologist 23.8 (2018): 943-947.
Liu, et al., "Corticosteroids do not influence the efficacy and kinetics of CAR-T cells for B-cell acute lymphoblastic leukemia", Blood Cancer J, (Jan. 2, 2020), vol. 10, No. 2, p. 15, 4 pages.
Maude, et al., "Managing Cytokine Release Syndrome Associated With Novel T Cell-Engaging Therapies", Cancer J, (Jan. 1, 2014), vol. 20, No. 2, pp. 119-122.
Frey, et al., "Refractory Cytokine Release Syndrome in Recipients of Chimeric Antigen Receptor (CAR) T Cells", Blood, (Jan. 1, 2014), p. 2296.
Reiff, "The use of anakinra in juvenile arthritis". Current Rheumatology Reports, 7: 434-440, 2005.

(56) References Cited

OTHER PUBLICATIONS

Teachey, et al., "Identification of Predictive Biomarkers for Cytokine Release Syndrome after Chimeric Antigen Receptor T-cell Therapy for Acute Lymphoblastic Leukemia", Cancer Discov., vol. 6, No. 6,(Apr. 13, 2016), pp. 664-679.
Tanaka, et al, "Therapeutic Targeting of the Interleukin-6 Receptor", Annual Review of Pharmacology and Toxicology., US, (Feb. 10, 2012), vol. 52, No. 1, pp. 199-219.
Trikha, et al, "Targeted anti-interleukin-6 monoclonal antibody therapy for cancer: a review of the rationale and clinical evidence", Clinical Cancer Research, (Oct. 15, 2003), vol. 9, No. 13, pp. 4653-4665.
Vadhan-Raj, et al., "A randomized trial of a single-dose rasburicase versus five-daily doses in patients at risk for tumor lysis syndrome", Annals of Oncology 23, 1640-1645, 2012.
Wagner et al., "CAR T Cell Therapy for Solid Tumors: Bright Future or Dark Reality?", Mol Ther, (Nov. 4, 2020), vol. 28, No. 11, pp. 2320-2339.
Weber et al., "Interleukin-1 (IL-1) Pathway" Sci Signal. Jan. 19, 2010;3(105):cm1.
Zhang, et al. "Etanercept as a new therapeutic option for cytokine release syndrome following chimeric antigen receptor T cell therapy." Experimental Hematology & Oncology 10 (2021): 1-4.
Evidence showing that Martin, et al. was published online on Apr. 14, 2012.
Fujiwara et al. "Hinge and Transmembrane Domains of Chimeric Antigen Receptor Regulate Receptor Expression and Signaling Threshold." Cells, May 9, 2020; 9 (5): 1182; pp. 1-17.
PCT request form of PCT/US2013/050267 filed Jul. 12, 2013.
Wikipedia entry for "Cytokine Storm" archived by www.archive.org on Jun. 5, 2012.
Evidence that Wikipedia entry for "Cytokine Storm" was archived on Jun. 5, 2012 by www.archive.org.
Wikipedia entry for "Cytokine Storm" archived by Wikipedia on May 6, 2012.
Patentees' submission in European Patent Appl. No. 18154090.7, Feb. 25, 2019, 2 pages.
Patentees' submission in European Patent Appl. No. 18154090.7, Feb. 12, 2018, 2 pages.
Wikipedia entry for Methotrexate, dated May 24, 2021.
Wikipedia entry for Ciclosporin, dated May 24, 2021.
Inventor's Assignment of Invention to The Children's Hospital of Philadelphia in U.S. Appl. No. 61/782,982.
Inventor's Assignment of Invention to The Trustees of the University of Pennsylvania in U.S. Appl. No. 61/671,482 and U.S. Appl. No. 61/671,482.
Inventor's Assignment of Invention to The Children's Hospital of Philadelphia in U.S. Appl. No. 61/671,482.
Inventor's Assignment of Invention to The Trustees of the University of Pennsylvania in U.S. Appl. No. 61/671,482.
University of Pennsylvania Intellectual Property Participation Agreement signed by Bruce Levine on May 7, 2012.
Patent and Tangible Research Property Policies and Procedures of the University of Pennsylvania made effective as of Jul. 1, 2010.

* cited by examiner

TOXICITY MANAGEMENT FOR ANTI-TUMOR ACTIVITY OF CARS

CROSS-REFERENCE TO RELATED APPLICATION

The present application is a continuation of U.S. patent application Ser. No. 19/233,446, filed on Jun. 10, 2025, which is a continuation of abandoned U.S. patent application Ser. No. 18/937,759, filed on Nov. 5, 2024, which is a continuation of abandoned U.S. patent application Ser. No. 17/677,208, filed on Feb. 22, 2022, which is a continuation of U.S. patent application Ser. No. 15/963,728, issued as U.S. Pat. No. 11,273,219, filed on Apr. 26, 2018, which is a continuation of abandoned U.S. patent application Ser. No. 14/410,659, filed on Dec. 23, 2014, which is a U.S. national phase application filed under 35 U.S.C. § 371 claiming benefit to International Patent Application No. PCT/US2013/050267 filed on Jul. 12, 2013, which is entitled to priority under 35 U.S.C. § 119(e) to U.S. Provisional Application No. 61/671,482, filed on Jul. 13, 2012 and U.S. Provisional Application No. 61/782,982, filed on Mar. 14, 2013, each of which is hereby incorporated by reference in its entirety.

SEQUENCE LISTING

The instant application contains a Sequence Listing which has been submitted electronically in ST.26 XML format and is hereby incorporated by reference in its entirety. Said ST.26 copy, created on Nov. 3, 2025, is named PAT055411_ST26_SL.xml and is 2,000 bytes in size.

BACKGROUND OF THE INVENTION

Patients with relapsed and chemotherapy-refractory acute lymphocytic leukemia (ALL) have a poor prognosis despite the use of aggressive therapies such as allogeneic hematopoietic stem cell transplantation (Barrett et al., 1994, N Engl J Med 331:1253-8; Gokbuget et al., 2012, Blood 120:2032-41) and bi-specific CD19 antibody fragments (Bargou et al., 2008, Science 321:974-7). Chimeric antigen receptor modified T cells targeting lineage-specific antigens CD19 and CD20 have been reported to be effective in adults with CLL and B-cell lymphomas (Till et al., 2008, Blood 112:2261-71; Kochenderfer et al., 2010, Blood 116:4099-102; Brentjens et al., 2011, Blood 118:4817-28; Porter et al., 2011, N Engl J Med 365:725-33; Kalos et al., 2011, Science Translational Medicine 3:95ra73; Savoldo et al., 2011, J Clin Invest 121:1822-5). However, the effects of CAR T cells on ALL blasts, a more immature leukemia with a more rapid progression, have not been fully investigated.

Delayed onset of the tumor lysis syndrome and cytokine secretion, combined with vigorous in vivo chimeric antigen receptor T-cell expansion has been reported (Porter et al., 2011, N Engl J Med 365:725-33; Kalos et al., 2011, Science Translational Medicine 3:95ra73). However, the effects of cytokine secretion and disorders associated with in vivo chimeric antigen recept T-cell expansion have not been fully investigated.

Thus, there is an urgent need in the art for compositions and methods for treatment of cancer using CARs and addressing toxicity of the CARs. The present invention addresses this need.

SUMMARY OF THE INVENTION

The invention provides a method of treating a patient having a disease, disorder or condition associated with an elevated expression of a tumor antigen. In one embodiment, the method comprises administering a first-line therapy and a second-line therapy to a patient in need thereof, wherein the first line therapy comprises administering to the patient an effective amount of a cell genetically modified to express a CAR, wherein the CAR comprises an antigen binding domain, a transmembrane domain, and an intracellular signaling domain.

In one embodiment, following the administration of the first-line therapy, cytokine levels in the patient are monitored to determine the appropriate type of second-line therapy to be administered to the patient and the appropriate second-line therapy is administered to the patient in need thereof.

In one embodiment, an increase in the level of a cytokine identifies a type of cytokine inhibitory therapy to be administered to the patient in need thereof.

In one embodiment, the cytokine is selected from the group consisting of IL-1β, IL-2, IL-4, IL-5, IL-6, IL-8, IL-10, IL-12, IL-13, IL-15, IL-17, IL-1Ra, IL-2R, IFN-α, IFN-γ, MIP-1α, MIP-1β, MCP-1, TNFα, GM-CSF, G-CSF, CXCL9, CXCL10, CXCR factors, VEGF, RANTES, EOTAXIN, EGF, HGF, FGF-β, CD40, CD40L, ferritin, and any combination thereof.

In one embodiment, the cytokine inhibitory therapy is selected from the group consisting of a small interfering RNA (siRNA), a microRNA, an antisense nucleic acid, a ribozyme, an expression vector encoding a transdominant negative mutant, an antibody, a peptide, a small molecule, a cytokine inhibitory drug, and any combination thereof.

In one embodiment, the cytokine levels are monitored by detecting the protein level of the cytokine in a biological sample from the patient.

In one embodiment, the cytokine levels are monitored by detecting the nucleic acid level of the cytokine in a biological sample from the patient.

The invention provides a method of reducing or avoiding an adverse effect associated with the administration of a cell genetically modified to express a CAR, wherein the CAR comprises an antigen binding domain, a transmembrane domain, and an intracellular signaling domain, the method comprising monitoring the levels of a cytokine in a patient to determine the appropriate type of cytokine therapy to be administered to the patient and administering the appropriate cytokine therapy to the patient.

In one embodiment, an increase in the level of a cytokine identifies a type of cytokine inhibitory therapy to be administered to the patient.

In one embodiment, the cytokine is selected from the group consisting of IL-10, IL-2, IL-4, IL-5, IL-6, IL-8, IL-10, IL-12, IL-13, IL-15, IL-17, IL-1Ra, IL-2R, IFN-α, IFN-γ, MIP-1α, MIP-1β, MCP-1, TNFα, GM-CSF, G-CSF, CXCL9, CXCL10, CXCR factors, VEGF, RANTES, EOTAXIN, EGF, HGF, FGF-β, CD40, CD40L, ferritin, and any combination thereof.

In one embodiment, the cytokine inhibitory therapy is selected from the group consisting of a small interfering RNA (siRNA), a microRNA, an antisense nucleic acid, a ribozyme, an expression vector encoding a transdominant negative mutant, an intracellular antibody, a peptide, a small molecule, a cytokine inhibitory drug, and any combination thereof.

In one embodiment, the cytokine levels are monitored by detecting the protein level of the cytokine in a biological sample from the patient.

In one embodiment, the cytokine levels are monitored by detecting the nucleic acid level of the cytokine in a biological sample from the patient.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A shows two children with multiply-relapsed chemotherapy-refractory CD19+ B cell precursor acute lymphoblastic leukemia who were treated with CTL019 cells, infused on Day 0. Changes in serum lactate dehydrogenase (LDH) and body temperature after CTL019 infusion, with maximum temperature per 24 hour period demarcated with circles. CHOP-100 was given methylprednisolone starting on day 5 at 2 mg/kg/day, tapered to off by day 12. On the morning of day 7, etanercept was given 0.8 mg/kg×1. At 6 μm in the evening of day 7, tocilizumab 8 mg/kg×1 was administered. A transient improvement in pyrexia occurred with administration of corticosteroids on day 5 in CHOP-100, with complete resolution of fevers occurring after administration of cytokine-directed therapy consisting of etanercept and tocilizumab on day 8. FIG. 4B shows serum cytokines and inflammatory markers measured at frequent time points after CTL019 infusion. Cytokine values are shown using a semi-logarithmic plot with fold-change from baseline. Baseline (Day 0 pre-infusion) values (pg/ml serum) for each analyte were (CHOP-100, CHOP-101): IL1-β: (0.9, 0.2); IL-6: (4.3, 1.9); TNF-α: (1.5, 0.4); IL2Rα: (418.8, 205.7); IL-2: (0.7, 0.4); IL-10 (9.9, 2.3); IL1Rα: (43.9, 27.9). Both patients developed pronounced elevations in a number of cytokines and cytokine receptors, including soluble interleukin 1A and 2 receptor (IL-1RA and IL-2R), interleukins 2, 6 and 10 (IL-2, IL-6 and IL-10), tumor necrosis factor-α (TNF-α), and interferon-γ (INF-γ). FIG. 4C shows changes in circulating absolute neutrophil count (ANC), absolute lymphocyte count (ALC) and white blood cell (WBC) count. Of note, the increase in the ALC was primarily composed of activated CT019 T lymphocytes.

FIG. 5A shows flow cytometric analysis of peripheral blood stained with antibodies to detect CD3 and the anti-CD19 CAR. Depicted are the percent of CD3 cells expressing the CAR in CHOP-100 and CHOP-101. FIG. 5B shows the presence of CTL019 T cells in peripheral blood, bone marrow, and CSF by quantitative real-time PCR. Genomic DNA was isolated from whole blood, bone marrow aspirates and CSF collected at serial time points before and after CTL019 infusion. FIG. 5C shows flow cytometric detection of CTL019 cells in CSF collected from CHOP-100 and CHOP-101. FIG. 5D shows images of activated large granular lymphocytes in Wright-stained smears of the peripheral blood and cytospins of the CSF.

FIG. 9A shows persistent B cell aplasia in CHOP-100. The top panel shows a predominant population of leukemic blast cells in bone marrow aspirated from CHOP-100 expressing CD19 and CD20 on day +6. This population is absent at day +23 and 6 months. FIG. 9B shows B cell aplasia and emergence of CD19 escape variant cells in CHOP-101. Flow cytometric analysis of bone marrow aspirates from CHOP-101 stained with anti-CD45, CD34 and CD19. In the bottom row, side scatter and the CD45 dim positive cells were used to identify leukemic cells that express variable amounts of CD34 and CD19 at baseline. Only CD19 negative blasts were detected on day 64. Numerical values in the top panel represent the fraction of the total leukocytes represented in each quadrant. Numerical values in the lower panel represent the percentage from the total leukocytes represented in the CD45dim/SS low gate.

DETAILED DESCRIPTION

Figure 1:
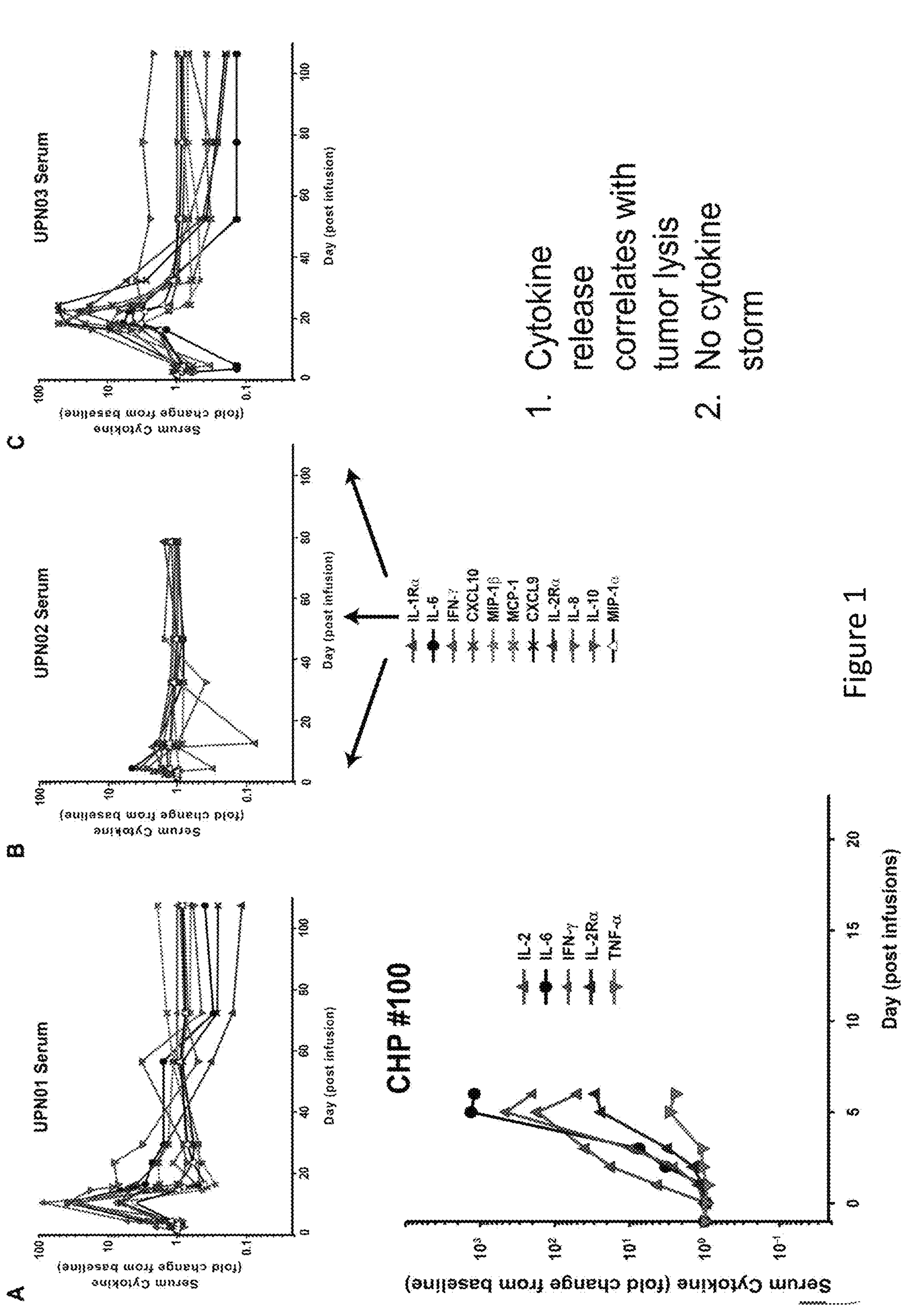
FIG. 1 is an image demonstrating serum cytokine levels in four different patients. All patients exhibited cytokine release, including IL-6.

The invention relates to compositions and methods for treating cancer including but not limited to hematologic malignancies and solid tumors. The invention also encompasses methods of treating and preventing certain types of cancer, including primary and metastatic cancer, as well as cancers that are refractory or resistant to conventional chemotherapy. The methods comprise administering to a patient in need of such treatment or prevention a therapeutically or prophylactically effective amount of a T cell transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

As part of the overall treatment regimen, the invention encompasses methods of managing certain cancers (e.g., preventing or prolonging their recurrence, or lengthening the time of remission) by evaluating the profile of soluble factors in patients post T cell infusion. Preferably, the profile of soluble factors includes evaluation of a cytokine profile. When the cytokine profile indicates an increase in a particular cytokine post T cell infusion compared to pre T cell infusion, a skilled artisan can elect to administer to the patient in need of such management an effective amount of a cytokine inhibitory compound or a pharmaceutically acceptable salt, solvate, hydrate, stereoisomer, clathrate, or pro drug thereof to manage the elevated levels of the cytokine post T cell infusion.

The present invention is partly based on the discovery that the identify of a unique combination of factors whose modulation from baseline or pre-existing levels at baseline can help track T cell activation, target activity, and potential harmful side effects following CAR T cell infusion in order to help manage the treatment of the cancer. Exemplary factors include but are not limited to IL-1β, IL-2, IL-4, IL-5, IL-6, IL-8, IL-10, IL-12, IL-13, IL-15, IL-17, IL-1Ra, IL-2R, IFN-α, IFN-γ, MIP-1α, MIP-1β, MCP-1, TNFα, GM-CSF, G-CSF, CXCL9, CXCL10, CXCR factors, VEGF, RANTES, EOTAXIN, EGF, HGF, FGF-β, CD40, CD40L, ferritin, and the like.

The present invention relates to a strategy of adoptive cell transfer of T cells transduced to express a chimeric antigen receptor (CAR) in combination with toxicity management, where a profile of soluble factors from a post T cell infusion patient is generated and a therapy directed against the elevated soluble factor is carried out in order to treat the cancer. For example, generating a real time soluble factor profile allows for intervention of the elevated soluble factors with the appropriate inhibitor in order to bring the levels down to normal levels.

In one embodiment, the CAR of the invention comprises an extracellular domain having an antigen recognition domain that targets a desired antigen, a transmembrane domain, and a cytoplasmic domain. The invention is not limited to a specific CAR. Rather, any CAR that targets a desired antigen can be used in the present invention. Compositions and methods of making CARs have been described in PCT/US 11/64191, which is incorporated by reference in its entirety herein.

In one embodiment, the CAR of the invention comprises a CD19 antigen binding domain, a transmembrane domain, a costimulatory signaling region, and a CD3 zeta signaling domain, wherein the CD19 antigen binding domain comprises the light chain variable region and the heavy chain variable region of SEQ ID NO: 1 (DIQMTQTTSSL-SASLGDRVTISCRASQDISKY-LNWYQQKPDGTVKLLIYHTSR LHSGVPSRFSGSGSGTDYSLTISNLEQEDI-ATYFCQQGNTLPYTFGGGTKLEIT GGGGSGGGGSGGGGSEVKLQESGPGLVAP-SQSLSVTCTVSGVSLPDYGVSWI RQPPRKGLEW-LGVIWGSETTYYN-SALKSRLTIIKDNSKSQVFLKMNSLQTDDT AIYYCAKHYYYGGSYAMDYWGQGTSVTVSS), and the costimulatory signaling region comprises a 4-1BB signaling domain or a CD28 signaling domain.

In some embodiments of any of the methods above, the methods result in a measurable reduction in tumor size or evidence of disease or disease progression, complete response, partial response, stable disease, increase or elongation of progression free survival, increase or elongation of overall survival, or reduction in toxicity.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

"Activators" or "agonists" of a soluble factor are used herein to refer to molecules of agents capable of activating or increasing the levels of the soluble factor. Activators are compounds that increase, promote, induce activation, activate, or upregulate the activity or expression of soluble factor, e.g., agonists. Assays for detecting activators include, e.g., expressing the soluble factor in vitro, in cells, or cell membranes, applying putative agonist compounds, and then determining the functional effects on activity of the soluble factor, as described elsewhere herein.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are often tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term “antibody fragment” refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term “antigen” or “Ag” as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an “antigen” as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a “gene” at all. It is readily apparent that an antigen can be generated synthesized or can be derived from a biological sample. Such a biological sample can include, but is not limited to a tissue sample, a tumor sample, a cell or a biological fluid.

The term “auto-antigen” means, in accordance with the present invention, any self-antigen which is recognized by the immune system as if it were foreign. Auto-antigens comprise, but are not limited to, cellular proteins, phosphoproteins, cellular surface proteins, cellular lipids, nucleic acids, glycoproteins, including cell surface receptors.

The term “autoimmune disease” as used herein is defined as a disorder that results from an autoimmune response. An autoimmune disease is the result of an inappropriate and excessive response to a self-antigen. Examples of autoimmune diseases include but are not limited to, Addision’s disease, alopecia greata, ankylosing spondylitis, autoimmune hepatitis, autoimmune parotitis, Crohn’s disease, diabetes (Type I), dystrophic epidermolysis bullosa, epididymitis, glomerulonephritis, Graves’ disease, Guillain-Barr syndrome, Hashimoto’s disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren’s syndrome, spondyloarthropathies, thyroiditis, vasculitis, vitiligo, myxedema, pernicious anemia, ulcerative colitis, among others.

As used herein, the term “autologous” is meant to refer to any material derived from the same individual to which it is later to be re-introduced into the individual.

“Allogeneic” refers to a graft derived from a different animal of the same species.

“Xenogeneic” refers to a graft derived from an animal of a different species.

The term “cancer” as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, by “combination therapy” is meant that a first agent is administered in conjunction with another agent. “In conjunction with” refers to administration of one treatment modality in addition to another treatment modality.

As such, “in conjunction with” refers to administration of one treatment modality before, during, or after delivery of the other treatment modality to the individual. Such combinations are considered to be part of a single treatment regimen or regime. As used herein, the term “concurrent administration” means that the administration of the first therapy and that of a second therapy in a combination therapy overlap with each other.

“Co-stimulatory ligand,” as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A “co-stimulatory molecule” refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A “co-stimulatory signal,” as used herein, refers to a signal, which in combination with a primary signal, such as TCR/CD3 ligation, leads to T cell proliferation and/or upregulation or downregulation of key molecules.

A “disease” is a state of health of an animal wherein the animal cannot maintain homeostasis, and wherein if the disease is not ameliorated then the animal’s health continues to deteriorate. In contrast, a “disorder” in an animal is a state of health in which the animal is able to maintain homeostasis, but in which the animal’s state of health is less favorable than it would be in the absence of the disorder. Left untreated, a disorder does not necessarily cause a further decrease in the animal’s state of health.

An “effective amount” as used herein, means an amount which provides a therapeutic or prophylactic benefit.

As used herein “endogenous” refers to any material from or produced inside an organism, cell, tissue or system.

As used herein, the term "exogenous" refers to any material introduced to an organism, cell, tissue or system that was produced outside the organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Inhibitors" or "antagonists" of a soluble factor are used herein to refer to molecules of agents capable of inhibiting, inactivating or reducing the levels of the soluble factor. Inhibitors are compounds that, e.g., bind to, partially or totally block activity, decrease, prevent, delay activation, inactivate, desensitize, or down regulate the activity or expression of soluble factor, e.g., antagonists. Inhibitors include polypeptide inhibitors, such as antibodies, soluble receptors and the like, as well as nucleic acid inhibitors such as siRNA or antisense RNA, genetically modified versions of the soluble factor, e.g., versions with altered activity, as well as naturally occurring and synthetic soluble factor antagonists, small chemical molecules and the like. Assays for detecting inhibitors include, e.g., expressing the soluble factor in vitro, in cells, or cell membranes, applying putative antagonist compounds, and then determining the functional effects on activity of the soluble factor, as described elsewhere herein.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The phrase "level of a soluble factor" in a biological sample as used herein typically refers to the amount of protein, protein fragment or peptide levels of the soluble factor that is present in a biological sample. A "level of a soluble factor" need not be quantified, but can simply be detected, e.g., a subjective, visual detection by a human, with or without comparison to a level from a control sample or a level expected of a control sample.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

A "transplant," as used herein, refers to cells, tissue, or an organ that is introduced into an individual. The source of the transplanted material can be cultured cells, cells from another individual, or cells from the same individual (e.g., after the cells are cultured in vitro). Exemplary organ transplants are kidney, liver, heart, lung, and pancreas.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating cancer in a patient. In one embodiment, the treatment method comprises a first-line of therapy comprising administering the CAR of the invention into the patient to induce an anti-tumor immune response and monitoring the levels of soluble factors in the patient post T cell infusion to determine the type of second-line of therapy appropriate to treat the patient as a consequence of the first-line of therapy.

In one embodiment, the second-line of therapy comprises evaluating the profile of soluble factors in a patient following receipt of an infusion of the appropriate CAR T (referred elsewhere herein as "post T cell infusion") where when the soluble factor profile indicates an increase in a particular soluble factor post T cell infusion compared to pre T cell infusion, a skilled artisan can elect to administer to the patient in need of an effective amount of a soluble factor inhibitory compound in order to manage the elevated levels of the soluble factor post T cell infusion. Accordingly, the second-line of therapy in one embodiment includes administering a type of soluble factor inhibitory therapy to manage the elevated levels of certain soluble factor s resulting from the first-line of therapy of using CAR T cells.

In yet another embodiment, the second-line of therapy relating to administering a soluble factor inhibitory compound to the patient can be combined with other conventionally therapies used to treat, prevent or manage diseases or disorders associated with, or characterized by, undesired angiogenesis. Examples of such conventional therapies include, but are not limited to, surgery, chemotherapy, radiation therapy, hormonal therapy, biological therapy and immunotherapy.

In one embodiment, the CAR of the invention can be engineered to comprise an extracellular domain having an antigen binding domain that targets tumor antigen fused to an intracellular signaling domain of the T cell antigen receptor complex zeta chain (e.g., CD3 zeta). An exemplary tumor antigen B cell antigen is CD19 because this antigen is expressed on malignant B cells. However, the invention is not limited to targeting CD19. Rather, the invention includes any tumor antigen binding moiety. The antigen binding moiety is preferably fused with an intracellular domain from one or more of a costimulatory molecule and a zeta chain. Preferably, the antigen binding moiety is fused with one or more intracellular domains selected from the group of a CD137 (4-1BB) signaling domain, a CD28 signaling domain, a CD3zeta signal domain, and any combination thereof.

In one embodiment, the CAR of the invention comprises a CD137 (4-1BB) signaling domain. This is because the present invention is partly based on the discovery that CAR-mediated T-cell responses can be further enhanced with the addition of costimulatory domains. For example, inclusion of the CD137 (4-1BB) signaling domain significantly increased CAR mediated activity and in vivo persistence of CAR T cells compared to an otherwise identical CAR T cell not engineered to express CD137 (4-1BB). However, the invention is not limited to a specific CAR. Rather, any CAR that targets a tumor antigen can be used in the present invention. Compositions and methods of making and using CARs have been described in PCT/US 11/64191, which is incorporated by reference in its entirety herein.

METHODS

The treatment regimen of the invention result in a measurable reduction in tumor size or evidence of disease or disease progression, complete response, partial response, stable disease, increase or elongation of progression free survival, increase or elongation of overall survival, or reduction in toxicity.

As part of the overall treatment regimen, the invention encompasses a first-line and a second-line therapy, wherein the first-line therapy comprises administering a CAR T cell of the invention to the patient in need thereof. The treatment regimen of the invention allows for the management of the cancer and treatment thereof by evaluating the soluble factor profile in patients post T cell infusion. An appropriate second-line therapy comprises administering an appropriate soluble factor inhibitor to the patient in order to reduce the elevated levels of the soluble factor resulting from the first-line therapy. In some instances, the appropriate second-line therapy comprises administering an appropriate soluble factor activator to the patient in order to increase the suppressed levels of the soluble factor resulting from the first-line therapy.

In one embodiment, an appropriate second-line therapy comprises administering an appropriate cytokine inhibitor to the patient in order to reduce the elevated levels of the cytokine resulting from the first-line therapy. In some instances, the appropriate second-line therapy comprises administering an appropriate cytokine activator to the patient in order to increase the suppressed levels of the cytokine resulting from the first-line therapy.

In one embodiment, differential levels are over expression (high expression) or under expression (low expression) as compared to the expression level of a normal or control cell, a given patient population, or with an internal control. In some embodiments, levels are compared between the patient and a normal individual, between the patient post T cell infusion and pre T cell infusion, or between the patient post T cell infusion at a first time point and a second time point.

In one embodiment, the invention includes evaluating differential levels of one or more cytokines to generate a cytokine profile in a patient post T cell infusion in order to determine the type of cytokine therapy to be applied to the patient for the purpose of regulating the cytokine level back to normal levels. The invention may therefore be applied to identify cytokine levels elevated as a result of the presence of the CAR T cells of the invention in the patient, which allows the specialized treatment of the patient with cytokine inhibitors to decrease the elevated levels of the cytokine. In another embodiment, invention may be applied to identify cytokine levels decreased as a result of the presence of the CAR T cells of the invention in the patient, which allows the specialized treatment of the patient with cytokine activators to increase the diminished levels of the cytokine.

In one embodiment, cytokines levels that are elevated as a result of receiving a CAR T cell infusion include but are not limited to IL-10, IL-2, IL-4, IL-5, IL-6, IL-8, IL-10, IL-12, IL-13, IL-15, IL-17, IL-1 Ra, IL-2R, IFN-α, IFN-γ, MIP-1α, MIP-1β, MCP-1, TNFα, GM-CSF, G-CSF, CXCL9, CXCL10, CXCR factors, VEGF, RANTES, EOTAXIN, EGF, HGF, FGF-β, CD40, CD40L, ferritin, and the like. However, the invention should not be limited to these listed cytokines. Rather, the invention includes any cytokine identified to be elevated in a patient as a result of receiving a CAR T cell infusion.

In one embodiment, cytokines levels that are decreased as a result of receiving a CAR T cell infusion include but are not limited to IL-1, IL-2, IL-4, IL-5, IL-6, IL-8, IL-10, IL-12, IL-13, IL-15, IL-17, IL-1Ra, IL-2R, IFN-α, IFN-γ, MIP-1α, MIP-1β, MCP-1, TNFα, GM-CSF, G-CSF, CXCL9, CXCL10, CXCR factors, VEGF, RANTES, EOTAXIN, EGF, HGF, FGF-β, CD40, CD40L, ferritin, and the like. However, the invention should not be limited to these listed cytokines. Rather, the invention includes any cytokine identified to be decreased in a patient as a result of receiving a CAR T cell infusion.

Detecting a Cytokine and Treatment Thereof

Although this section describes detection of a cytokine and treatment thereof as part of the second-line therapy, the invention encompasses detection of any soluble factor and treatment thereof as part of the second-line therapy. Therefore, the description in the context of a "cytokine" can equally be applied to a "soluble factor."

In one embodiment, as part of the second-line therapy, the invention includes methods of detecting levels of a cytokine in a patient that has received infusion of a CAR T cell of the invention. In some embodiments, the presence or level of a cytokine can be used to select a candidate treatment. In some other embodiments, the presence or levels of the cytokine can be used to determine the success during the course of or after treatment of the first-line, second-line, or both the first and second-line of therapy.

Biological samples in which the cytokine can be detected include, for example, serum. In some embodiments, biological samples include a tissue biopsy which may or may not have a liquid component.

Immunoassays can be used to qualitatively or quantitatively analyze the cytokine levels in a biological sample. A general overview of the applicable technology can be found in a number of readily available manuals, e.g., Harlow & Lane, Cold Spring Harbor Laboratory Press, Using Antibodies: A Laboratory Manual (1999).

In addition to using immunoassays to detect the levels of cytokines in a biological sample from a patient, assessment of cytokine expression and levels can be made based on the level of gene expression of the particular cytokines. RNA hybridization techniques for determining the presence and/or level of mRNA expression are well known to those of skill in the art and can be used to assess the presence or level of gene expression of the cytokine of interest.

In some embodiments, the methods of the present invention utilize selective binding partners of the cytokine to identify the presence or determine the levels of the cytokine in a biological sample. The selective binding partner to be used with the methods and kits of the present invention can be, for instance, an antibody. In some aspects, monoclonal antibodies to the particular cytokine can be used. In some other aspects, polyclonal antibodies to the particular cytokine can be employed to practice the methods and in the kits of the present invention.

Commercial antibodies to the cytokine are available and can be used with the methods and kits of the present invention. It is well known to those of skill in the art that the type, source and other aspects of an antibody to be used is a consideration to be made in light of the assay in which the antibody is used. In some instances, antibodies that will recognize its antigen target on a Western blot might not applicable to an ELISA or ELISpot assay and vice versa.

In some embodiments, the antibodies to be used for the assays of the present invention can be produced using techniques for producing monoclonal or polyclonal antibodies that are well known in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Such antibodies can be used for therapeutic and diagnostic applications, e.g., in the treatment and/or detection of any of the specific cytokine-associated diseases or conditions described herein.

Detection methods employing immunoassays are particularly suitable for practice at the point of patient care. Such methods allow for immediate diagnosis and/or prognostic evaluation of the patient. Point of care diagnostic systems are described, e.g., in U.S. Pat. No. 6,267,722 which is incorporated herein by reference. Other immunoassay formats are also available such that an evaluation of the biological sample can be performed without having to send the sample to a laboratory for evaluation. Typically these assays are formatted as solid assays where a reagent, e.g., an antibody is used to detect the cytokine. Exemplary test devices suitable for use with immunoassays such as assays of the present invention are described, for example, in U.S. Pat. Nos. 7,189,522; 6,818,455 and 6,656,745.

In some aspects, the present invention provides methods for detection of polynucleotide sequences which code for the cytokine in a biological sample. As noted above, a "biological sample" refers to a cell or population of cells or a quantity of tissue or fluid from a patient. Most often, the sample has been removed from a patient, but the term "biological sample" can also refer to cells or tissue analyzed in vivo, i.e., without removal from the patient. Typically, a "biological sample" will contain cells from the patient, but the term can also refer to noncellular biological material.

In one embodiment, amplification-based assays are used to measure the level of a desired cytokine. In such an assay, nucleic acid sequences of the desired cytokine act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the cytokine associated gene. Methods of quantitative amplification are well known to those of skill in the art. Detailed protocols for quantitative PCR are provided, e.g., in Innis et al. (1990) PCR Protocols, A Guide to Methods and Applications, Academic Press, Inc. N.Y.). RT-PCR methods are well known to those of skill (see, e.g., Ausubel et al., supra). In some embodiments, quantitative RT-PCR, e.g., a TaqMan™ assay, is used, thereby allowing the comparison of the level of mRNA in a sample with a control sample or value. The known nucleic acid sequences for a desired cytokine are sufficient to enable one of skill to routinely select primers to amplify any portion of the gene. Suitable primers for amplification of specific sequences can be designed using principles well known in the art (see, e.g., Dieffenfach & Dveksler, PCR Primer: A Laboratory Manual (1995)).

In some embodiments, hybridization based assays can be used to detect the amount of a desired cytokine in the cells of a biological sample. Such assays include dot blot analysis of RNA as well as other assays, e.g., fluorescent in situ hybridization, which is performed on samples that comprise cells. Other hybridization assays are readily available in the art.

In numerous embodiments of the present invention, the level and/or presence of a cytokine polynucleotide or polypeptide will be detected in a biological sample, thereby detecting the differential expression of the cytokine to generate a cytokine profile from a biological sample derived from a patient infused with a CAR T cell of the invention compared to the control biological sample.

The amount of a cytokine polynucleotide or polypeptide detected in the biological sample indicates the presence of a cytokine to generate a cytokine profile for the purpose of classifying the patient for the appropriate cytokine treatment. For example, when the cytokine profile indicates an increase in a particular cytokine post T cell infusion compared to control (e.g., pre T cell infusion), a skilled artisan can elect to administer to the patient in need of such management an effective amount of a cytokine inhibitory compound. Alternatively, when the cytokine profile indicates a decrease in a particular cytokine post T cell infusion compared to control (e.g., pre T cell infusion), a skilled artisan can elect to administer to the patient in need of such management an effective amount of a cytokine activator compound.

In some embodiments, the difference in cytokine levels between the post T cell infusion sample and the control sample and be at least about 0.5, 1.0, 1.5, 2, 5, 10, 100, 200, 500, 1000 fold.

The present methods can also be used to assess the efficacy of a course of treatment. For example, in a post T cell infusion patient containing an elevated amount of a cytokine IL-6, the efficacy of an anti-IL-6 treatment can be assessed by monitoring, over time, IL-6. For example, a reduction in IL-6 polynucleotide or polypeptide levels in a biological sample taken from a patient following a treatment, compared to a level in a sample taken from the mammal before, or earlier in, the treatment, indicates efficacious treatment.

In one embodiment, a treatment regimen can be based on neutralizing the elevated cytokine. For example, antagonists of a cytokine can be selected for treatment. Antibodies are an example of a suitable antagonist and include mouse antibodies, chimeric antibodies, humanized antibodies, and human antibodies or fragments thereof. Chimeric antibodies are antibodies whose light and heavy chain genes have been constructed, typically by genetic engineering, from immunoglobulin gene segments belonging to different species (see, e.g., Boyce et al., Annals of Oncology 14:520-535 (2003)). For example, the variable (V) segments of the genes from a mouse monoclonal antibody may be joined to human constant (C) segments. A typical chimeric antibody is thus a hybrid protein consisting of the V or antigen-binding domain from a mouse antibody and the C or effector regions from a human antibody.

Humanized antibodies have variable region framework residues substantially from a human antibody (termed an acceptor antibody) and complementarity determining regions substantially from a mouse-antibody, (referred to as the donor immunoglobulin). See Queen et al., Proc. NatL. Acad. Sci. USA 86:10029-10033 (1989) and WO 90/07861, U.S. Pat. Nos. 5,693,762, 5,693,761, 5,585,089, 5,530,101 and Winter, U.S. Pat. No. 5,225,539. The constant region(s), if present, are also substantially or entirely from a human immunoglobulin. Antibodies can be obtained by conventional hybridoma approaches, phage display (see, e.g., Dower et al., WO 91/17271 and McCafferty et al., WO 92/01047), use of transgenic mice with human immune systems (Lonberg et al., WO93/12227 (1993)), among other sources. Nucleic acids encoding immunoglobulin chains can be obtained from hybridomas or cell lines producing antibodies, or based on immunoglobulin nucleic acid or amino acid sequences in the published literature.

Other antagonists of a desired cytokine can also be used for treatment purposes. For example, a class of antagonists that can be used for the purposes of the present invention, are the soluble forms of the receptors for the cytokine. By way of merely illustrative purposes, an IL-6 antagonist is an anti-IL-6 antibody that specifically binds to IL-6. A specific antibody has the ability to inhibit or antagonize the action of IL-6 systemically. In some embodiments, the antibody binds IL-6 and prevents it from interacting with or activating its receptors (e.g. IL-6Rα or IL-6Rβ). In some embodiments, the activity of IL-6 can be antagonized by using an antagonist to the interleukin-6 receptors (IL-6R). U.S. Application number 2006251653 describes methods for treating interleukin-6 related disease and discloses a number of interleukin-6 antagonists including, for example, humanized anti-IL-6R antibodies and chimeric anti-IL-6R antibodies. In some embodiments, an IL-6 or IL-6R derivative can be used to block and antagonize the interaction between IL-6/IL-6R.

The invention is not limited to the cytokines and their corresponding activators and inhibitors described herein. Rather, the invention includes the used of any cytokine activator and/or inhibitor that is used in the art to modulate the cytokine. This is because the invention is based on managing cancer treatment in a patient receiving infusion of CAR T cells of the invention wherein the infused CAR T cells result in increase and decrease levels of various cytokines. One skilled in the art based on the disclosure presented herein that differential expression levels of a cytokine in a post T cell infusion sample compared to a control sample can be targeted for treatment for have the cytokine level be increased or decreased to normal levels.

Therapeutic Application

The present invention encompasses a cell (e.g., T cell) transduced with a lentiviral vector (LV). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the CART19 cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, a CART19 cells elicits an immune response specific against cells expressing CD19.

While the data disclosed herein specifically disclose lentiviral vector comprising anti-CD19 scFv derived from FMC63 murine monoclonal antibody, human CD8α hinge and transmembrane domain, and human 4-1BB and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like.

In one embodiment, the CAR can be designed to target CD33/IL3Ra to treat acute myelogenous leukemia and the like.

In one embodiment, the CAR can be designed to target c-Met to treat triple negative breast cancer, non-small cell lung cancer, and the like.

In one embodiment, the CAR can be designed to target PSMA to treat prostate cancer and the like.

In one embodiment, the CAR can be designed to target Glycolipid F77 to treat prostate cancer and the like.

In one embodiment, the CAR can be designed to target EGFRvIII to treat gliobastoma and the like.

In one embodiment, the CAR can be designed to target GD-2 to treat neuroblastoma, melanoma, and the like.

In one embodiment, the CAR can be designed to target NY-ESO-1 TCR to treat myeloma, sarcoma, melanoma, and the like.

In one embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

Treatment of Cytokine Release Syndrome (CRS)

The invention is based partly on the discovery that in vivo proliferation of CART19 cells and the potent anti-tumor activity associated therewith is also associated with with CRS, leading to hemophagocytic lymphohistiocytosis (HLH), also termed Macrophage Activation Syndrome (MAS). Without wishing to be bound by any particular theory, it is believed that that MAS/HLH is a unique biomarker that is associated with and may be required for CART19 potent anti-tumor activity.

Accordingly, the invention provides a first-line of therapy comprising administering the CAR of the invention into the patient and a second-line of therapy comprising administering a type of therapy to manage the elevated levels of certain soluble factors resulting from the first-line of therapy of using CAR T cells.

In one embodiment, the second-line of therapy comprises compositions and methods for the treatment of CRS. Symptoms of CRS include high fevers, nausea, transient hypotension, hypoxia, and the like. The present invention is based on the observation that CART19 cells induced elevated levels of soluble factors in the patient including but is not limited to IFN-γ, TNFα, IL-2 and IL-6. Therefore, the second-line of therapy comprises compounds and methods for neutralizing the effects against the elevated cytokines resulting from the administration of the CART19 cells. In one embodiment, the neutralizing agents are capable of counteracting undesired concerted burst of cytokine expression/activity and, thus, are useful for the prevention, amelioration and treatment of CRS associated with CART19 therapy.

In one embodiment, the treatment of CRS is performed around day 10-12 post-infusion of CART19 cells.

In one embodiment, the second-line of therapy comprises administering a steroid to the patient. In another embodiment, the second-line of therapy comprises administering one of more of a steroid, an inhibitor of TNFα, and an inhibitor of IL-6. An example of a TNFα inhibitor is entanercept. An example of an IL-6 inhibitor is Tocilizumab (toc).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Cytokine Therapy in Combination with CAR T Cell Infusion

Figure 2:
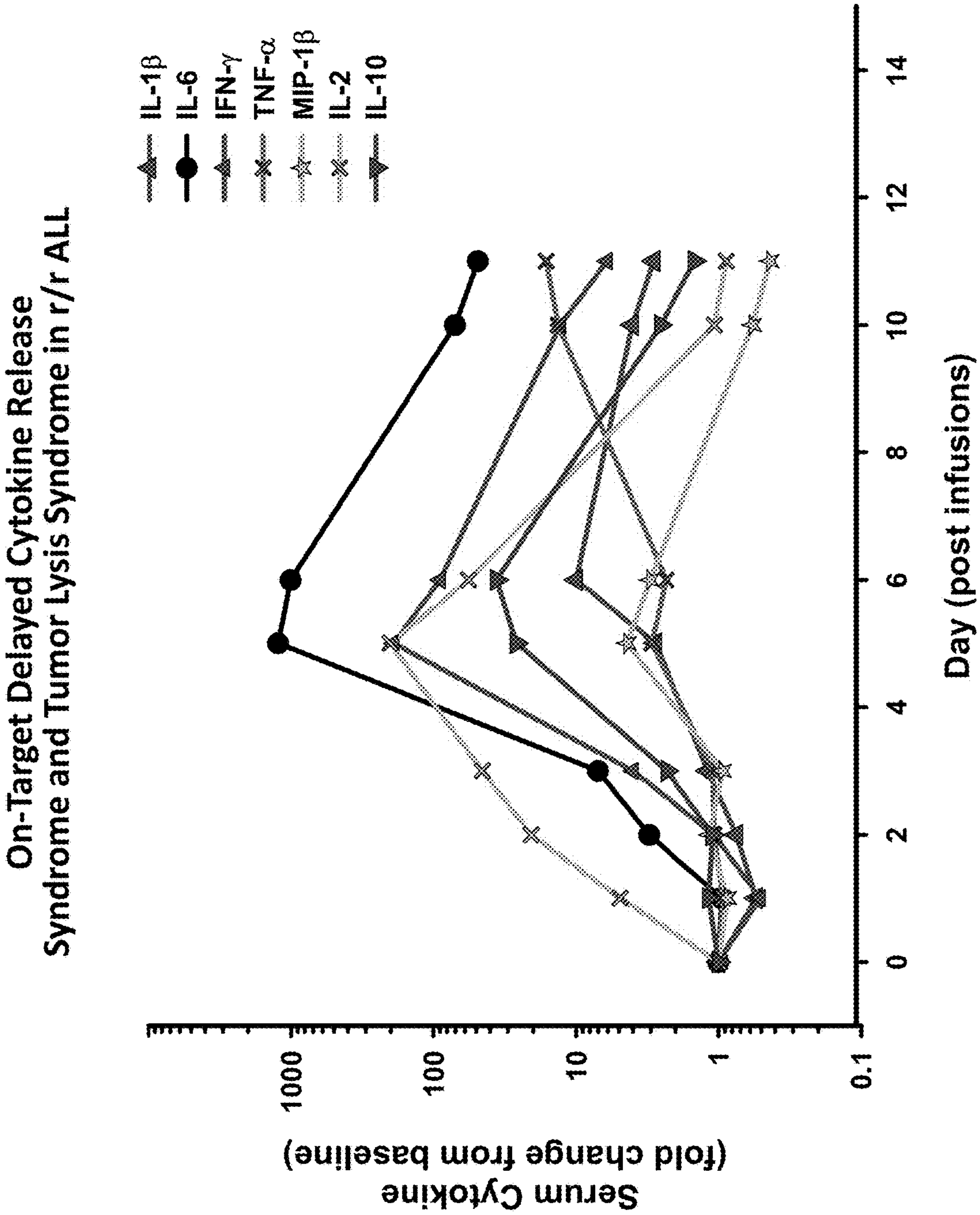
FIG. 2 is an image depicting serum cytokines plotted in a representative patient. The patient was critically ill on days 5 to 7, and only began to improve following tocilizumab administration.

The results presented herein demonstrate that patients following infusion of CAR T cells exhibit differential expression levels of various cytokines. In some instances, the elevated levels of some cytokines are a result of the toxicity of the infused CAR T cells (FIG. 1). It was observed that tocilizumab (anti-IL6) can ameliorate the toxicity of CARs and seemingly preserve antitumor effects in 2 of 2 patients (FIG. 2). Without wishing to be bound by any particular theory, it is believed that anakinra and other reagents that block IL-1 may also be useful in this regard. The data presented herein also demonstrates that IL-1 is elevated in patients, and this may lead to the later rise in IL-6. Anakinra is an IL-1Ra recombinant protein which binds to the IL1 receptors and blocks both IL-1 alpha and beta signaling. Anakinra has a short ½ life. There is an advantage to use Anakinra to start treating patients since both IL-1 alpha and beta would be blocked, and also relieve the cytokine storm and keep the anti-tumor effect.

Figure 3:
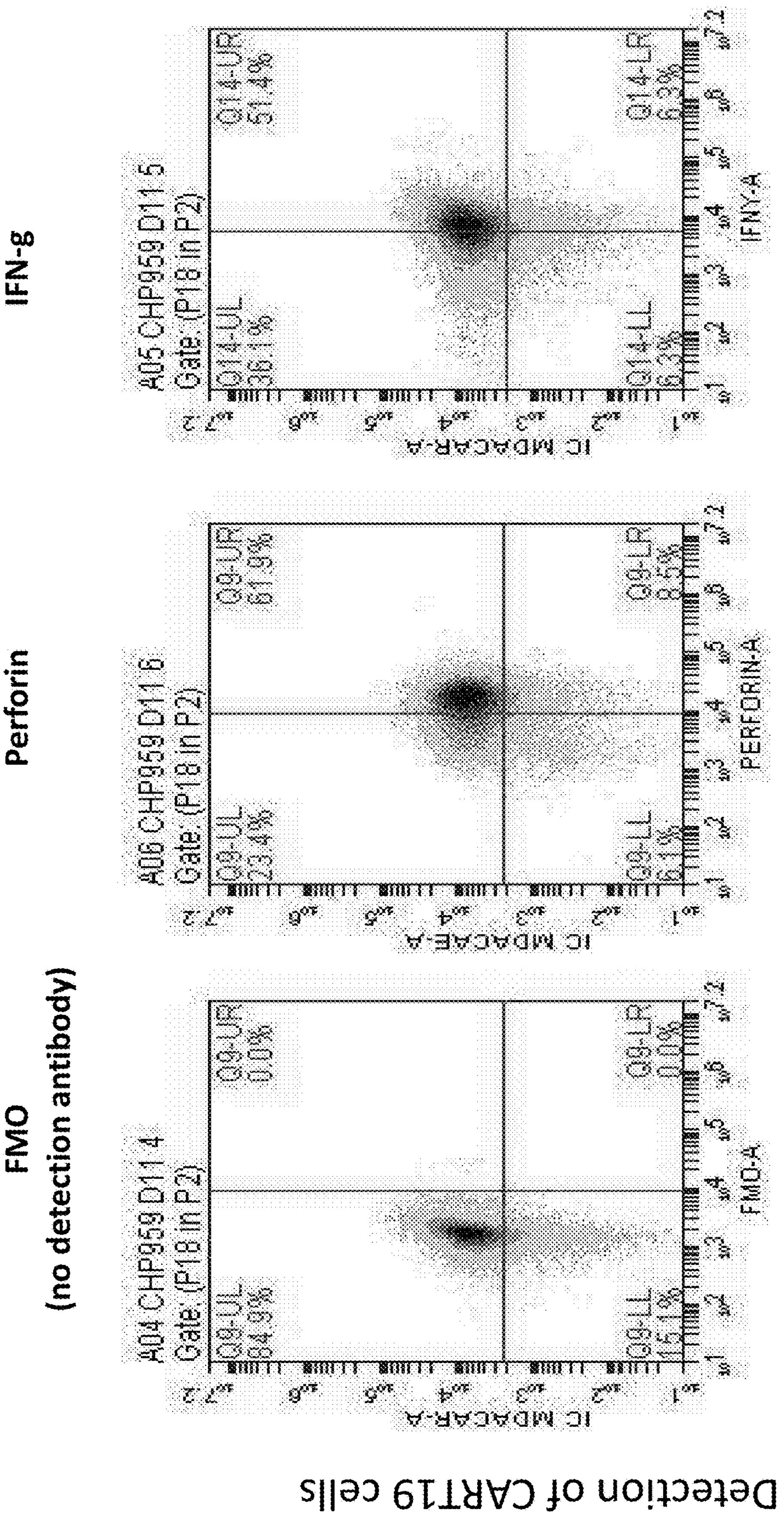
FIG. 3 is an image demonstrating that antibody interventions do not impact CART 19 cellular functionality as measured for markers of T cell activity (perforin and IFN-γ).

It was also observed that antibody interventions did not impart CART19 cellular functionality as measured by Perforin and IFN-γ (FIG. 3).

Example 2: CD19-Redirected Chimeric Antigen Receptor T (CART19) Cells Induce a Cytokine Release Syndrome (CRS) and Induction of Treatable Macrophage Activation Syndrome (MAS) that can be Managed by the IL-6 Antagonist Tocilizumab (Toc)

Infusion of CART19 cells results in 100 to 100,000× in vivo proliferation, tumor lysis syndrome followed by durable antitumor activity, and prolonged persistence in patients with B cell tumors. The results presented herein demonstrate that in vivo proliferation of CART19 cells and potent anti-tumor activity therefrom is associated with CRS, leading to hemophagocytic lymphohistiocytosis (HLH), also termed MAS. Without wishing to be bound by any particular theory, it is believed that MAS/HLH is a unique biomarker that is associated with and may be required for potent anti-tumor activity.

Autologous T cells were lentivirally transduced with a CAR composed of anti-CD19 scFv/4-1BB/CD3-zeta, activated/expanded ex-vivo with anti-CD3/anti-CD28 beads, and then infused into ALL or CLL patients with persistent disease after 2-8 prior treatments. CART19 anti ALL activity was also modeled in a xenograft mouse model with high level of human ALL/human T cell engraftment and simultaneous detection of CAR T cells and ALL using 2-color bioluminescent imaging.

The results presented herein provides updated results of 10 patients who received CART19 cells, including 9 patients with CLL and 1 pediatric patient with relapsed refractory ALL. 6/9 evaluable patient s had a complete recovery (CR) or partial recovery (PR), including 4 sustained CRs. While there was no acute infusional toxicity, all responding patients also developed CRS. All had high fevers, as well as grade 3 or 4 hypotension/hypoxia. CRS preceded peak blood expression of CART19 cells, and then increased in intensity until the CART19 cell peak (D10-31 after infusion). The ALL patient experienced the most significant toxicity, with grade 4 hypotension and respiratory failure. Steroid therapy on D6 resulted in no improvement. On D9, noting high levels of TNFα and IL-6 (peak increases above baseline: IFNγ at 6040×; IL-6 at 988×; IL-2R at 56×, IL-2 at 163× and TNFα at 17×), TNFα and IL-6 antagonists (entanercept and toc) were administered. This resulted in resolution of fever and hypotension within 12 hr and a rapid wean from ventilator support to room air. These interventions had no apparent impact on CART19 cell expansion or efficacy: peak of CAR T cells (2539 CAR+ cells/uL; 77% of CD3 cells by flow) occurred on D11, and D23 bone marrow showed CR with negative minimal residual disease (MRD), compared to her initial on-study marrow which showed 65% blasts. Although she had no history of CNS ALL, spinal fluid showed detectable CART19 cells (21 lymphs/mcL; 78% CAR+). At 4 mo post infusion, this patient remained in CR, with 17 CART19 cells/uL in the blood and 31% CAR+CD3 cells in the marrow.

Clinical assessment of subsequent responding patients shows all had evidence of MAS/HLH including dramatic elevations of ferritin and histologic evidence of HLH. Peak ferritin levels range from 44,000 to 605,000, preceding and continuing with peak T cell proliferation. Other consistent findings include rapid onset hepatosplenomegaly unrelated to disease and moderate DIC.

Subsequently, 3 CLL patients have also been treated with toc, also with prompt and striking resolution of high fevers, hypotension and hypoxia. One patient received toc on D10 and achieved a CR accompanied by CART19 expansion. Another patient had rapid resolution of CRS following toc administration on day 9 and follow up for response is too short. A 3rd CLL patient received toc on D3 for early fevers and had no CART-19 proliferation and no response.

To model the timing of cytokine blockade, xenografts using bioluminescent primary pediatric ALL were established and then treated with extra cells from the clinical manufacture. The CART19 cells proliferated and resulted in prolonged survival. Cytokine blockade prior to T cell infusion with toc and/or etanercept abrogated disease control with less in vivo proliferation of infused CART19 cells, confirming the result seen in the one patient given early toc (D3).

CART19 T cells can produce massive in-vivo expansion, long-term persistence, and anti-tumor efficacy, but can also induce significant CRS with features suggestive of MAS/HLH that responds rapidly to cytokine blockade. Given prior to initiation of significant CART19 proliferation, blockade of TNFα and/or IL-6 may interfere with proliferation and effector function, but if given at a point where cell proliferation is underway, toc may ameliorate the symptoms that have been observed that correlate with robust clinical responses.

Example 3 Remission of ALL by Chimeric Antigen Receptor-Expressing T Cells

The results presented herein demonstrate that CAR T cells have clinical activity in acute lymphocytic leukemia (ALL). Briefly, two pediatric patients with relapsed and refractory pre-B cell ALL were treated with $10^6$ to $10^7$/kg T cell transduced with anti-CD19 antibody and a T-cell signaling molecule (CTL019 CAR T cells; also referred to as CART19). The CTL019 T cells expanded more than 1000-fold in both patients, and trafficked to bone marrow. In addition, the CAR T cells were able to cross the blood brain barrier and persisted at high levels for at least 6 months, as measured in the cerebral spinal fluid. Eight severe adverse events were noted. Both patients developed a cytokine release syndrome (CRS) and B cell aplasia. In one child, the CRS was severe and cytokine blockade with etanercept and tocilizumab was effective in reversing the syndrome, and yet did not prevent CAR T cell expansion and anti-leukemic efficacy. Complete remission was observed in both patients, and is ongoing in one patient at 9 months after treatment. The other patient relapsed with blast cells that no longer express CD19 approximately 2 months after treatment.

The results presented herein demonstrate that CAR modified T cells are capable of killing even aggressive treatment refractory acute leukemia cells in vivo. The emergence of tumor cells that no longer express the target indicates a need to target other molecules in addition to CD19 in some patients with ALL.

The in vivo expansion and robust anti-leukemic effects of CTL019 (CART19) cells in 3 patients with CLL as been reported (Porter et al., 2011, N Engl J Med 365:725-33; Kalos et al., 2011, Science Translational Medicine 3:95ra73). CTL019 is a CAR that includes a CD137 (4-1BB) signaling domain and is expressed using lentiviral vector technology (Milone et al., 1009, Mol Ther 17:1453-64). The results presented herein demonstrate the use of CTL019 in 2 pediatric patients with refractory and relapsed ALL. Both patients had remission of leukemia, accompanied by robust expansion of CTL019 in vivo with trafficking to marrow and the CNS. The anti-leukemic effects were potent since one patient had chemotherapy refractory disease precluding allogeneic donor stem cell transplantation and the other patient relapsed after allogeneic cord blood transplantation and was resistant to blinatumomab (chimeric bispecific anti-CD3 and anti-CD19) therapy.

The materials and methods employed in these experiments are now described.

MATERIALS AND METHODS

CART19

CTL019 (CART19) production has been previously reported (Porter et al., 2011, N Engl J Med 365:725-33; Kalos et al., 2011, Science Translational Medicine 3:95ra73). CTL019 was detected and quantified in patient specimens as previously reported (Porter et al., 2011, N Engl J Med 365:725-33; Kalos et al., 2011, Science Translational Medicine 3:95ra73).

Sample Draws and Processing

Samples (peripheral blood, bone marrow) were collected in lavender top (K2EDTA) or red top (no additive) vacutainer tubes (Becton Dickinson). Lavender top tubes were delivered to the laboratory within 2 hours of draw, or shipped overnight at room temperature in insulated containers essentially as described (Olson et al., 2011, J Transl Med 9:26) prior to processing. Samples were processed within 30 minutes of receipt according to established laboratory SOP. Peripheral blood and marrow mononuclear cells were purified, processed, and stored in liquid nitrogen as described (Kalos et al., 2011, Science Translational Medicine 3:95ra73). Red top tubes were processed within 2 hours of draw including coagulation time; serum isolated by centrifugation, aliquoted in single use 100 L aliquots and stored at −80° C. CSF was delivered to the laboratory within 30 minutes of aspiration and cells in CSF were collected by centrifugation of CSF fluid and processed for DNA and flow cytometry.

Q-PCR Analysis

Whole-blood or marrow samples were collected in lavender top (K2EDTA) BD vacutainer tubes (Becton Dickinson). Genomic DNA was isolated directly from whole-blood and Q-PCR analysis on genomic DNA samples was performed in bulk using ABI Taqman technology and a validated assay to detect the integrated CD19 CAR transgene sequence as described (Kalos et al., 2011, Science Translational Medicine 3:95ra73) using 200 ng genomic DNA per time-point for peripheral blood and marrow samples, and 18-21.7 ng genomic DNA per time-point for CSF samples. To determine copy number per unit DNA, an 8-point standard curve was generated consisting of 5 to $10^6$ copies CTL019 lentivirus plasmid spiked into 100 ng non-transduced control genomic DNA. Each data-point (sample, standard curve) was evaluated in triplicate with a positive Ct value in 3/3 replicates with % CV less than 0.95% for all quantifiable values. A parallel amplification reaction to control for the quality of interrogated DNA was performed using 20 ng input genomic DNA from peripheral blood and marrow (2-4.3 ng for CSF samples), and a primer/probe combination specific for non-transcribed genomic sequence upstream of the CDKN1A gene as described (Kalos et al., 2011, Science Translational Medicine 3:95ra73). These amplification reactions generated a correction factor (CF) to correct for calculated versus actual DNA input. Copies of transgene per microgram DNA were calculated according to the formula: copies calculated from CTL019 standard curve per input DNA (ng)×CF×1000 ng. Accuracy of this assay was determined by the ability to quantify marking of the infused cell product by Q-PCR. These blinded determinations generated Q-PCR and flow marking values of 11.1% and 11.6%, respectively, for the CHOP-100 and 20.0% and 14.4%, respectively, marking for the CHOP-101 infusion products.

Soluble Factor Analysis

Whole blood was collected in red top (no additive) BD vacutainer tubes (Becton Dickinson), processed to obtain serum using established laboratory SOP, aliquoted for single use and stored at −80° C. Quantification of soluble cytokine factors was performed using Luminex bead array technology and kits purchased from Life technologies (Invitrogen). Assays were performed as per the manufacturer protocol with a 9 point standard curve generated using a 3-fold dilution series. The 2 external standard points were evaluated in duplicate and the 5 internal standards in singlicate; all samples were evaluated in duplicate at 1:2 dilution; calculated % CV for the duplicate measures were less than 15%. Data were acquired on a FlexMAP-3D by percent and analyzed using XPonent 4.0 software and 5-parameter logistic regression analysis. Standard curve quantification ranges were determined by the 80-120% (observed/expected value) range. Reported values included those within the standard curve range and those calculated by the logistic regression analysis.

Antibody Reagents

The following antibodies were used for these studies: MDA-CAR (Jena and Cooper, 2013, L. Anti-idiotype antibody for CD19. PlosONE 2013; in press), a murine antibody to CD19 CAR conjugated to Alexa647. Antibodies for multi-parametric immunophenotyping: T cell detection panels: anti-CD3-FITC, anti-CD8-PE, anti-CD14-PE-Cy7, anti-CD16-PE-Cy7, anti-CD19-PE-Cy7 anti-CD16-PE-Cy7. B cell detection panels: anti-CD20-FITC, anti-CD45-PE, anti-CD45-APC, anti-CD19-PE-Cy7, anti-CD19-PE, anti-CD34-PCP-e710 and anti CD34-APC were procured from e-Biosciences.

Multi-Parameter Flow Cytometry

Cells were evaluated by flow cytometry directly after Ficoll-Paque processing, with the exception of the CHOP-101 baseline sample which was evaluated immediately after thaw of a cryopreserved sample. Multi-parametric immunophenotyping for peripheral blood and marrow samples was performed using approximately 0.2-0.5×$10^6$ total cells per condition (depending on cell yield in samples), and for CSF samples using trace amounts of cells collected following centrifugation of CSF fluid, and using fluorescence minus one (FMO) stains as described in the text. Cells were stained in 100 μL PBS for 30 minutes on ice using antibody and reagent concentrations recommended by the manufacturer, washed, and resuspended in 0.5% paraformaldehyde and acquired using an Accuri C6 cytometer equipped with a Blue (488) and Red (633 nm) laser. Accuri files were exported in FCS file format and analyzed using FlowJo software (Version 9.5.3, Treestar). Compensation values were established using single antibody stains and BD compensation beads (Becton Dickinson) and were calculated by the software. The gating strategy for T cells was as follows: Live cells (FSC/SSC)>dump channel (CD14+CD16+CD19-PECy7) vs CD3+>CD3+. The general gating strategy for B cells was as follows: Live cells (FSC/SSC)>SSC low events >CD19+. More gating details for the CHOP-100 and CHOP-101 samples are described in the individual Figures.

Molecular MRD Analysis

Molecular MRD analysis was performed by Adaptive Biotechnologies (Seattle, WA) and high-throughput next-generation sequencing of the BCR IGH CDR3 region using the Illumina HiSeq/MiSeq platform-based immunoSEQ assay (Larimore et al., 2012, J Immunol 189:3221-30). For these analyses, 701-6,000 ng (approximately 111,000-950,000 genome equivalents) of genomic DNA isolated from whole blood or marrow samples obtained from patients were subjected to combined multiplex PCR and sequencing followed by algorithmic analyses to quantify individual IGH CDR3 sequences in samples. Parallel amplifications and sequencing of the TCRB CDR3 region (Robins et al., 2009, Blood 114:4099-107) in each sample were done to assess quality of DNA samples. For each patient, the IGH CDR3 nucleotide sequences assayed from samples of different time points were aligned using EMBL-EBI multiple sequence alignment tool (Goujon et al., 2010, Nucleic Acids Res 38:W695-9; Sievers et al., 2011, Mol Syst Biol 7:539). The dominant clone from the earliest time-point sample was bioinformatically tracked across the assayed IGH CDR3 sequences in the following time-point samples to identify presence of sequences with 95% or greater pair-wise sequence identity. The total sequencing reads for those sequences similar to the dominant clone are reported for each time-point.

The results of the experiments are now described.

Case Reports

CHOP-100 was a 7 yo girl in her second recurrence of ALL. She was diagnosed 2 years prior and achieved a minimal residual disease (MRD) negative remission, relapsing 17 months after diagnosis. She re-entered remission after reinduction chemotherapy but recurred 4 months later, after which she did not respond to furtheclofaribine/etoposide/cyclophosphamide. Her karyotype at baseline was 48,XX, del(9)(p21.3), +11,del(14)(q2?q24), +16/46,XX[4]. Peripheral blood mononuclear cells (PBMC) were collected by apheresis before the intensive chemotherapy, anticipating that there may be insufficient circulating T cells available for cell manufacturing after such intensive treatment. This patient was infused with CTL019 cells that had been anti-CD3/CD28 expanded and lentivirally transduced to express the anti-CD19 CAR in a total dose of $3.8\times10^8$ cells/kg ($1.2\times10^7$ CTL019 cells/kg) given over 3 consecutive days as previously described (Porter et al., 2011, N Engl J Med 365:725-33; Kalos et al., 2011, Science Translational Medicine 3:95ra73). She did not receive lymphodepleting chemotherapy before her CTL019 infusions, with the most recent cytotoxic therapy given 6 weeks before CTL019 infusion. No immediate infusional toxicities were noted, but she was hospitalized for low-grade fevers which progressed to high fevers by day 4, and on day 5 the patient was transferred to the pediatric ICU (CHOP-100, FIG. 4A). This was followed by rapid progression to significant respiratory and cardiovascular compromise requiring mechanical ventilation and blood pressure support.

Figure 7:
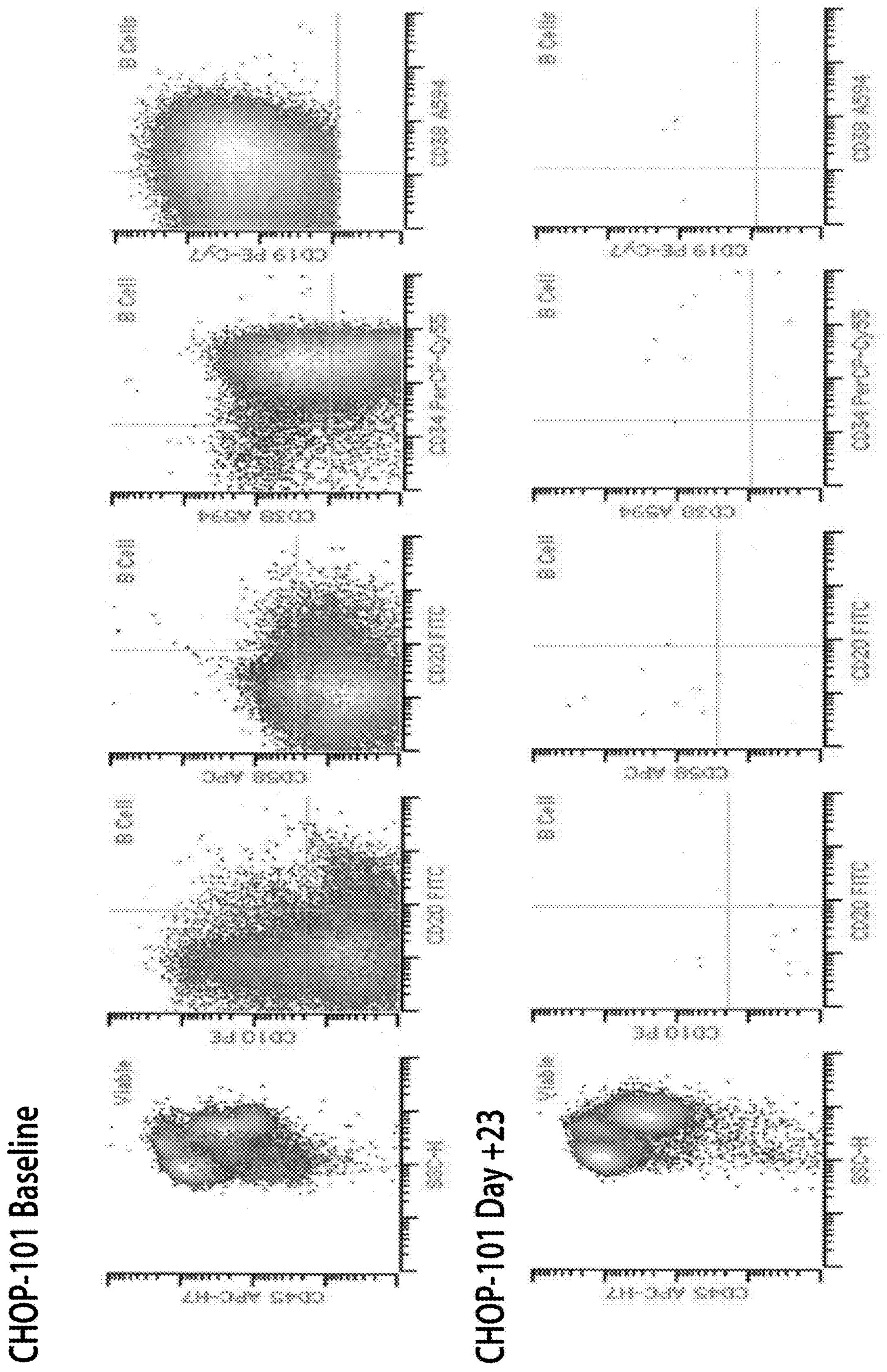
FIG. 7 is an image showing induction of remission in bone marrow in CHOP-101 on day +23 after CTL019 infusion. Clinical immunophenotyping report for CHOP-101 at baseline (Top panel) and at day +23 (Bottom panel). Cells were stained for CD10, CD19, CD20, CD34, CD38 and CD58. Flow cytometry was done after lysis of the red blood cells. The report on day +23 indicated that the white blood cells consisted of 42.0% lymphocytes, 6.0% monocytes, 50.3% myeloid forms, 0.17% myeloid blasts and no viable lymphoid progenitors. There was no convincing immunophenotypic evidence of residual precursor B cell lymphoblastic leukemia/lymphoma by flow cytometry. Essentially no viable B cells were identified.

The second ALL patient was a 10 yo girl (CHOP-101) who had experienced her second relapse after a 4/6 matched unrelated umbilical cord transplant 28 months after diagnosis and 10 months before CTL019 infusion. She had experienced graft vs. host disease (GVHD) after her transplant, which resolved with treatment; she was off immunosuppression at the time of her relapse. She did not subsequently re-enter remission in spite of multiple cytotoxic and biologic therapies. Her baseline karyotype was 46 XX, del(1)(p13), t(2;9)(q?21; q?21), t(3;17)(p24; q23), del(6)(q16q21), del (9)(q13q22), der(16)t(1;?;16)(p13;?p13.3)[9],//46, Xy[1]. Before PBMC collection, she was treated with two cycles of blinatumomab (Bargou et al., 2008, Science 321:974-7) with no response. Her peripheral blood cells were 68% donor origin at the time of PBMC collection. CTL019 T cells were manufactured and infused as a total dose of $10^7$ cells/kg ($1.4\times10^6$ CTL019 cells/kg) in a single dose, after etoposide/cyclophosphamide chemotherapy given for lymphodepletion the week before. Her bone marrow on the day before CTL019 infusion was replaced by a population of CD19+/CD34+ ALL cells, with variable expression of CD19 by standard clinical flow cytometry (FIG. 7). She had no immediate infusional toxicities, but developed a fever on D+6 and was admitted to the hospital. She experienced no cardiopulmonary toxicities, and did not receive glucocorticoids or anti-cytokine therapy. CHOP-101 experienced fever of unknown origin, suspected to be due to cytokine release (FIG. 4B), myalgias and two days of confusion (grade 3), which spontaneously resolved. She had no evidence of GVHD after the infusion of the CTL019 cells. Though these cells had been collected from the patient, they were largely of donor (cord blood) origin.

Induction of Remission in Both Subjects

Figure 4A:
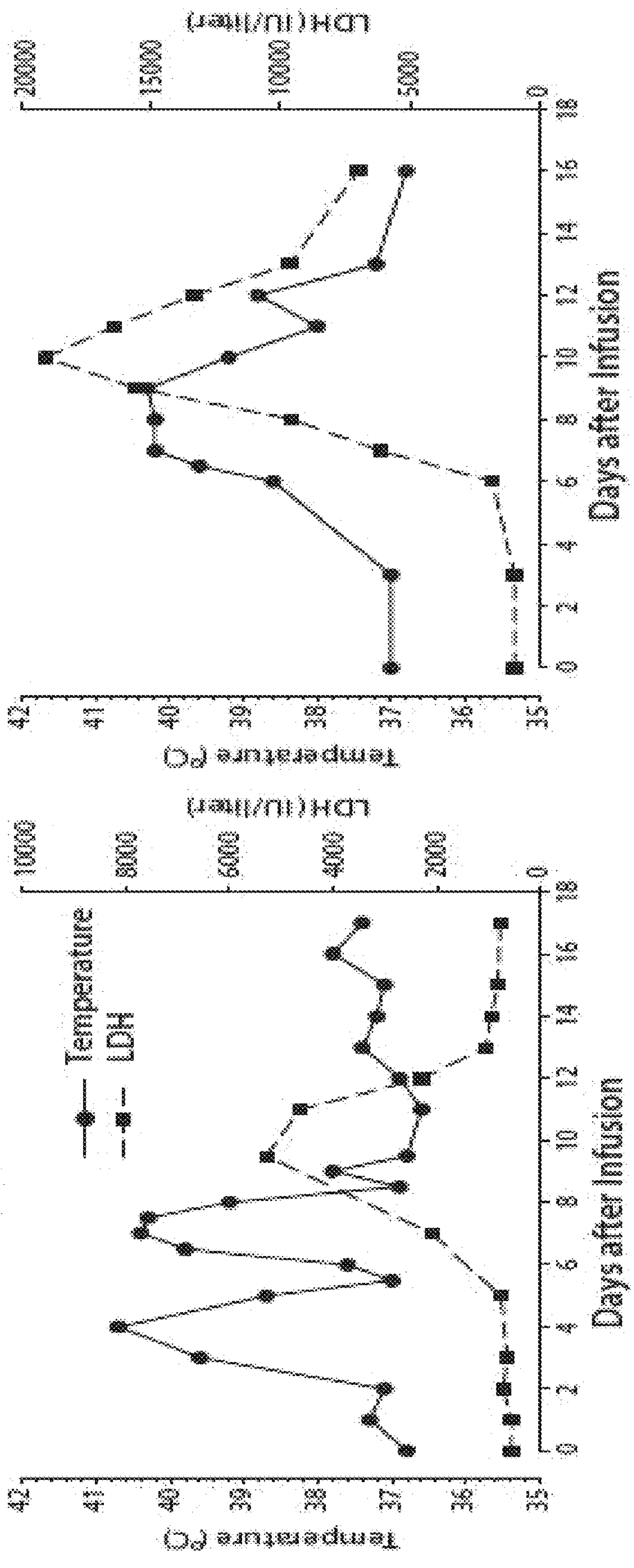
FIGS. 4A through 4C are images depicting clinical responses.
Figure 4B:
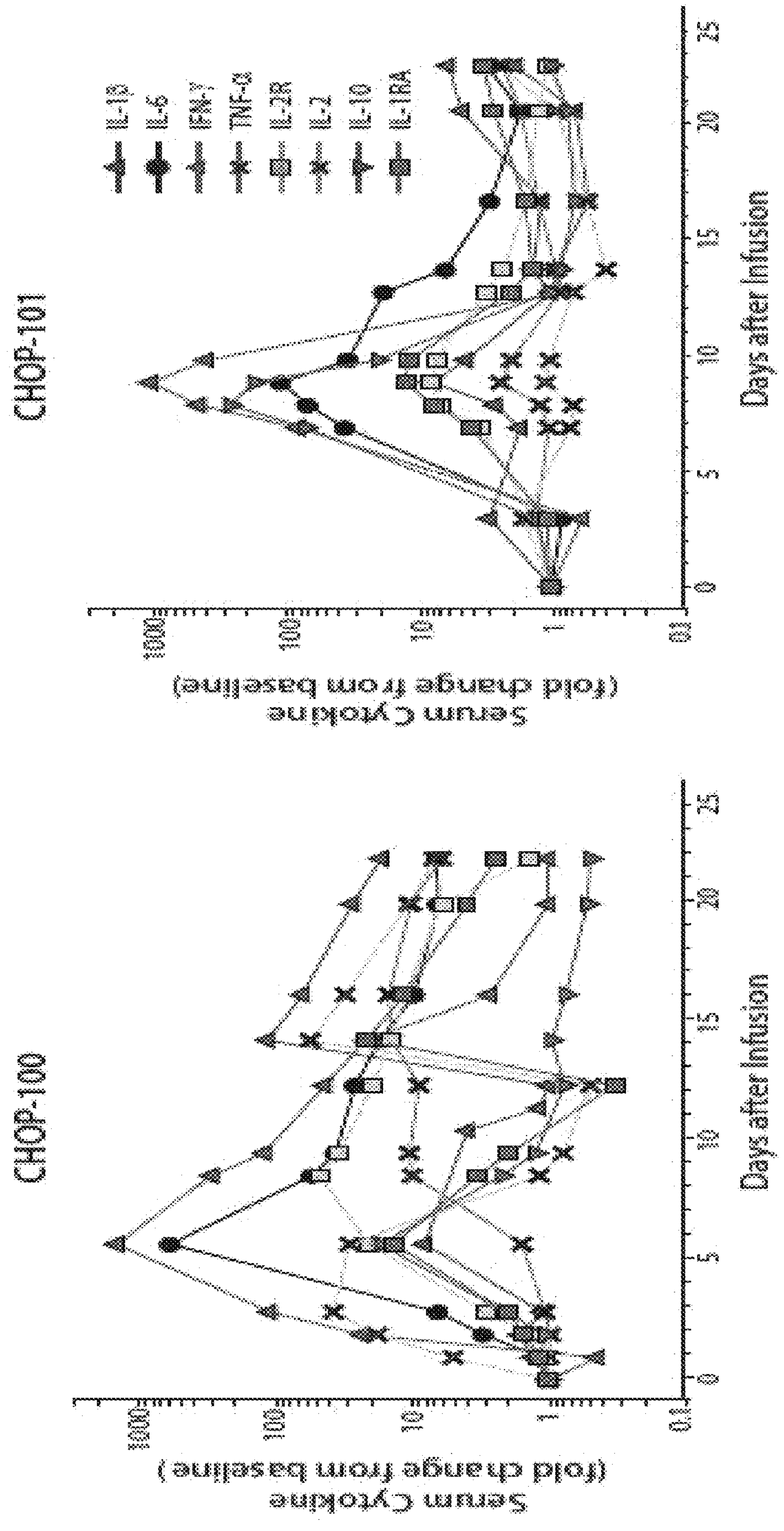
Figure 4C:
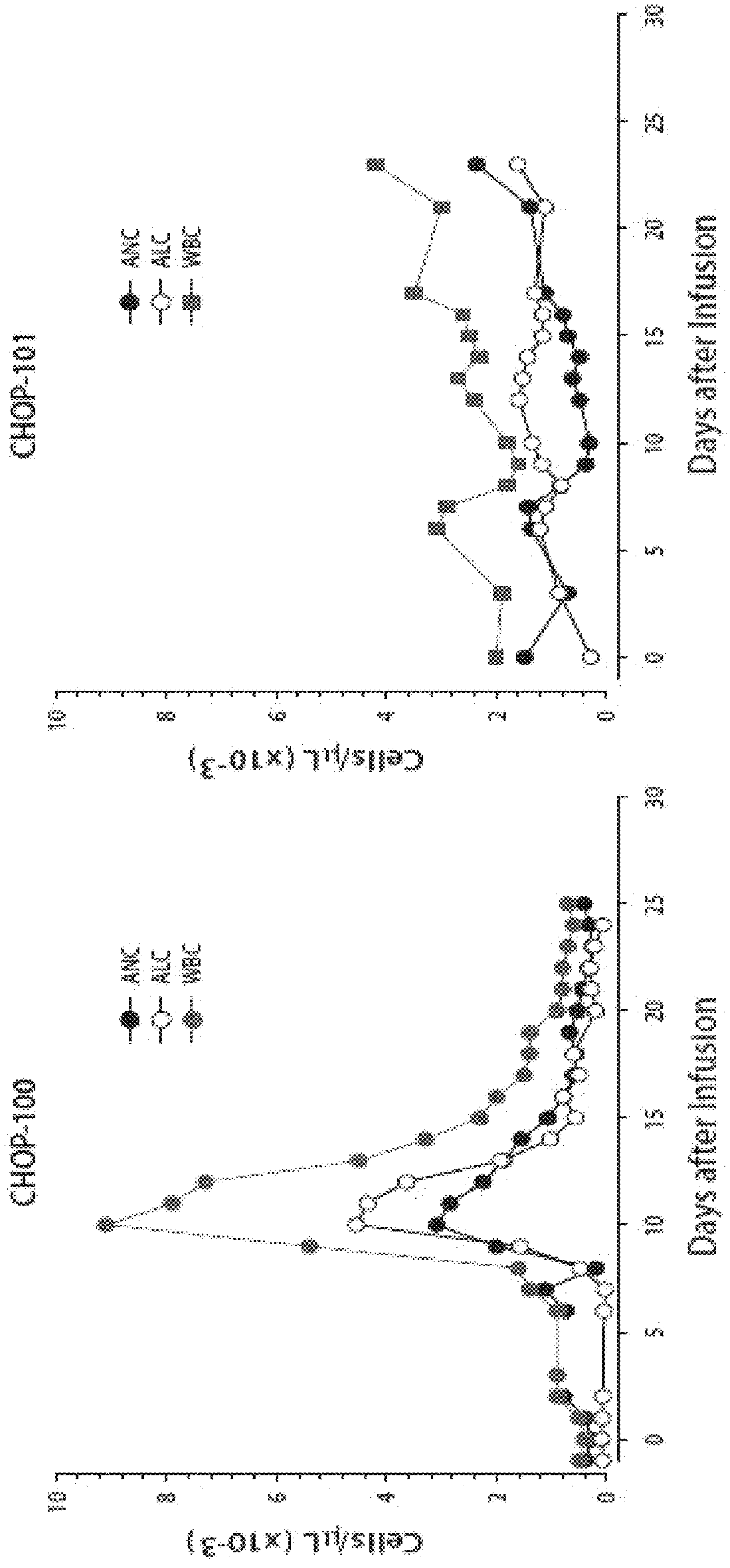
Figure 8:
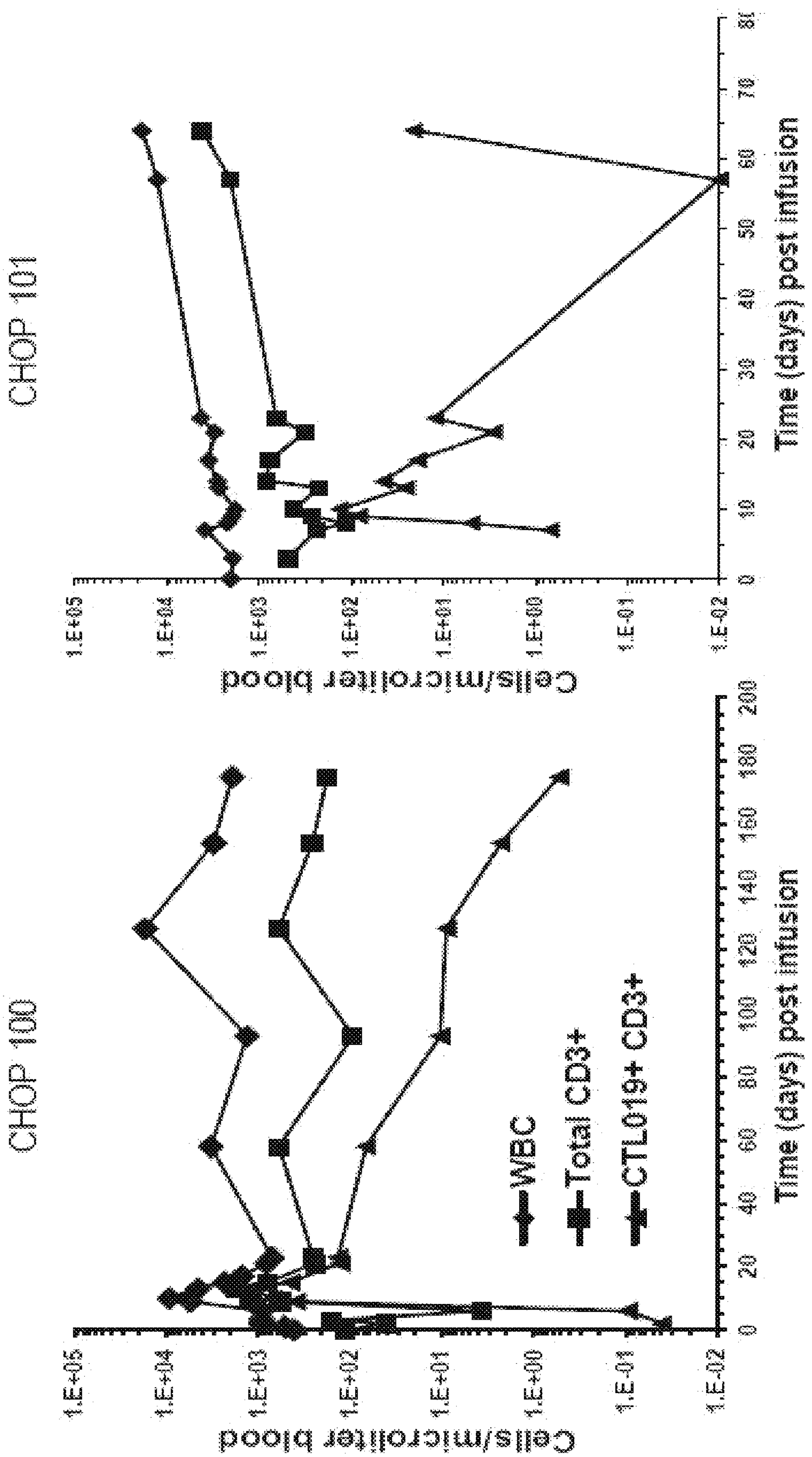
FIG. 8 is an image depicting in vivo expansion and persistence of CTL019 cells in blood. The number of white blood cells (WBC), CD3+ T cells, and CTL019 cells in blood is shown for CHOP-100 and CHOP-101. Cell numbers are shown on a semi-logarithmic plot.

Both subjects had an increase in circulating lymphocytes and neutrophils in the 2 weeks following CTL019 infusion, as shown by plots depicting total WBC, ALC, and ANC relative to timing of CTL019 infusion (FIG. 4C). Most of the lymphocytes were comprised of T cells that expressed the chimeric antigen receptor (FIG. 8), shown in more detail in FIGS. 5A-5D. In both subjects, high-grade non-infectious fevers were documented, followed by elevations of LDH (FIG. 4A). The elevations of LDH and high grade fevers were similar to those previously described in CLL patients after CTL019 infusion (Porter et al., 2011, N Engl J Med 365:725-33; Kalos et al., 2011, Science Translational Medicine 3:95ra73). Approximately one month after infusion, MRD negative (<0.01%) morphologic remission of leukemia was achieved in both subjects (Table 1).

The clinical remission in CHOP-100 was associated with a deep molecular remission that has persisted for at least 9 months as of January 2013 (Table 1). High-throughput DNA sequencing of the IGH locus revealed a pronounced decrease in total IGH reads at D+23 in the blood and marrow of CHOP-100. The malignant clone was not detected in the blood or marrow in more than 1 million cell equivalents that were sequenced at D+180. In contrast, T-cell receptor sequences were readily detected in blood and marrow, indicating the integrity of the DNA tested at all timepoints.

TABLE 1

Induction of molecular remission in blood and bone marrow of CHOP-100 and 101

| Patient | Tissue | Timepoint (day) | Number of input genomes (cell equivalents) | Total TCRβ reads | Total IGH reads | Total IGH unique reads | Dominant clone reads | Tumor clone frequency (%) |
|---|---|---|---|---|---|---|---|---|
| CHP959-100 | Blood | −1 | 111,340 | 525,717 | 189 | 6 | 185 | 97.88 |
| | | 23 | 218,210 | 1,651,129 | 0 | 0 | 0 | 0.00 |
| | | 87 | 288,152 | 1,416,378 | 0 | 0 | 0 | 0.00 |
| | | 180 | 420,571 | 1,276,098 | 6 | 2 | 0 | 0.00 |
| | Marrow | −1 | 317,460 | 348,687 | 59,791 | 318 | 59,774 | 99.97 |
| | | 23 | 362,819 | 1,712,507 | 37 | 2 | 33 | 89.19 |
| | | 87 | 645,333 | 425,128 | 10 | 1 | 10 | 100.00 |
| | | 180 | 952,381 | 800,670 | 45 | 7 | 0 | 0.00 |
| CHP959-101 | Blood | −1 | 152,584 | 1,873,116 | 38,170 | 52 | 30,425 | 79.71 |
| | | 23 | 417,371 | 1,462,911 | 92 | 5 | 18 | 19.60 |
| | Marrow | −1 | 158,730 | 2,417,992 | 66,368 | 65 | 50,887 | 74.43 |
| | | 23 | 305,067 | 1,978,600 | 1,414 | 11 | 946 | 66.90 |
| | | 60 | 916,571 | N/A | 530,833 | 206 | 363,736 | 68.90 |

Molecular analysis of minimal residual disease was performed on DNA isolated from whole blood or marrow Toxicity of CTL T19

Grade 3 and 4 adverse events are summarized in Table 2. Acute toxicity was observed in both patients that consisted of fever, and a cytokine release syndrome (CRS) that evolved into a macrophage activation syndrome (MAS). Both patients were monitored and given prophylaxis for tumor lysis syndrome. Both experienced substantial elevations of LDH, the causes of which were likely multifactorial but could have included tumor lysis syndrome. Each uric acid value in CHOP-100 was either below normal or in the normal range, and she received allopurinol only on days 5-6. CHOP-101 received prophylactic allopurinol on days 0-14 and had abnormal uric acid values of 4.8-5.7 on days 8-10, consistent with mild tumor lysis syndrome.

Both subjects developed prominent elevations in a number of cytokines and cytokine receptors in the serum (FIG. 1). In both patients, elevations in interferon-γ and IL-6 were most prominent. These observations are similar to the pattern observed previously in patients with CLL who also experienced remission of leukemia after CTL019 infusion (Kalos et al., 2011, Science Translational Medicine 3:95ra73). The peak cytokine elevations were temporally correlated with systemic inflammation as judged by changes in core body temperature (FIG. 4C).

TABLE 2

Adverse events (grade 3 and 4) in CHOP-100 and CHOP-101

| AE Category | AE Toxicity | AE Grade | AE Description | Duration |
|---|---|---|---|---|
| CHP959-100 | | | | |
| INFECTION | Febrile neutropenia | 3 | Febrile neutropenia. Temperature: Peak temperature 40.7° C., resolved day 7 after administration of tocilizumab. | 7 days |
| CARDIAC GENERAL | Hypotension | 4 | Shock requiring pressor support. Off all pressor support on day 7 other than weaning dobutamine | 4 days at grade 4, off all |
| VASCULAR | Acute vascular leak syndrome | 4 | Life-threatening; pressor support or ventilatory support indicated | see above |
| PULMONARY/UPPER RESPIRATORY | Adult Respiratory Distress Syndrome (ARDS) | 4 | Present, intubation indicated. Chest X-ray cleared on day 8. | 12 days |
| CHP959-101 | | | | |
| INFECTION | Febrile neutropenia | 3 | Febrile neuropenia. Peak temperature 40.3° C., resolved day 6 | 6 days |
| NEUROLOGY | Encephalopathy | 3 | Parents reported confusion. MRI was normal. | 3 days |
| METABOLIC/LABORATORY | elevated AST | 4 | Peak AST Value: 1060 (Grade 4) | 1 day at grade 4 |
| METABOLIC/LABORATORY | elevated ALT | 4 | Peak ALT Value: 748 (Grade 4) | 1 day at grade 4 |

Adverse events were graded according to Common Terminology Criteria for Adverse Events 3.0

In CHOP-100, glucocorticoids were administered on D+5 with a brief response in the fever curve but without remission of hypotension. A single course of anti-cytokine therapy consisting of etanercept and tocilizumab was given on D+8 and was followed by rapid clinical effects: within hours she defervesced, was weaned off vasoactive medications and ventilatory support as her clinical and radiologic ARDS resolved. She did not have laboratory evidence of a tumor lysis syndrome; however, biochemical evidence of MAS was noteed with elevation of ferritin to 45,529 ng/dl on D+11, coagulopathy with elevated d-dimer and hypofibrinogenemia, hepatosplenomegaly, elevation of transaminases, elevated LDH (FIG. 4C), and elevated triglycerides, as well as a cytokine profile consistent with MAS. Her ferritin decreased to 2,368 by D+26 and the clinical and laboratory abnormalities of MAS resolved.

In CHOP-101, although there was no direct evidence of a tumor lysis syndrome other than fever and changes in LDH (FIG. 4C), she also developed features of MAS with elevations in ferritin to 33,360 on D+7, peaking at 74,899 on day 11, transaminases that reached grade 4 for 1 day, and an elevated d-dimer in serum. These biochemical changes were reversible, as transaminases improved to grade 1 and the ferritin decreased to 3,894 by D+21. She was discharged from the hospital on day D+16.

In Vivo Expansion of CTL019 in Patients with ALL

Figure 5A:
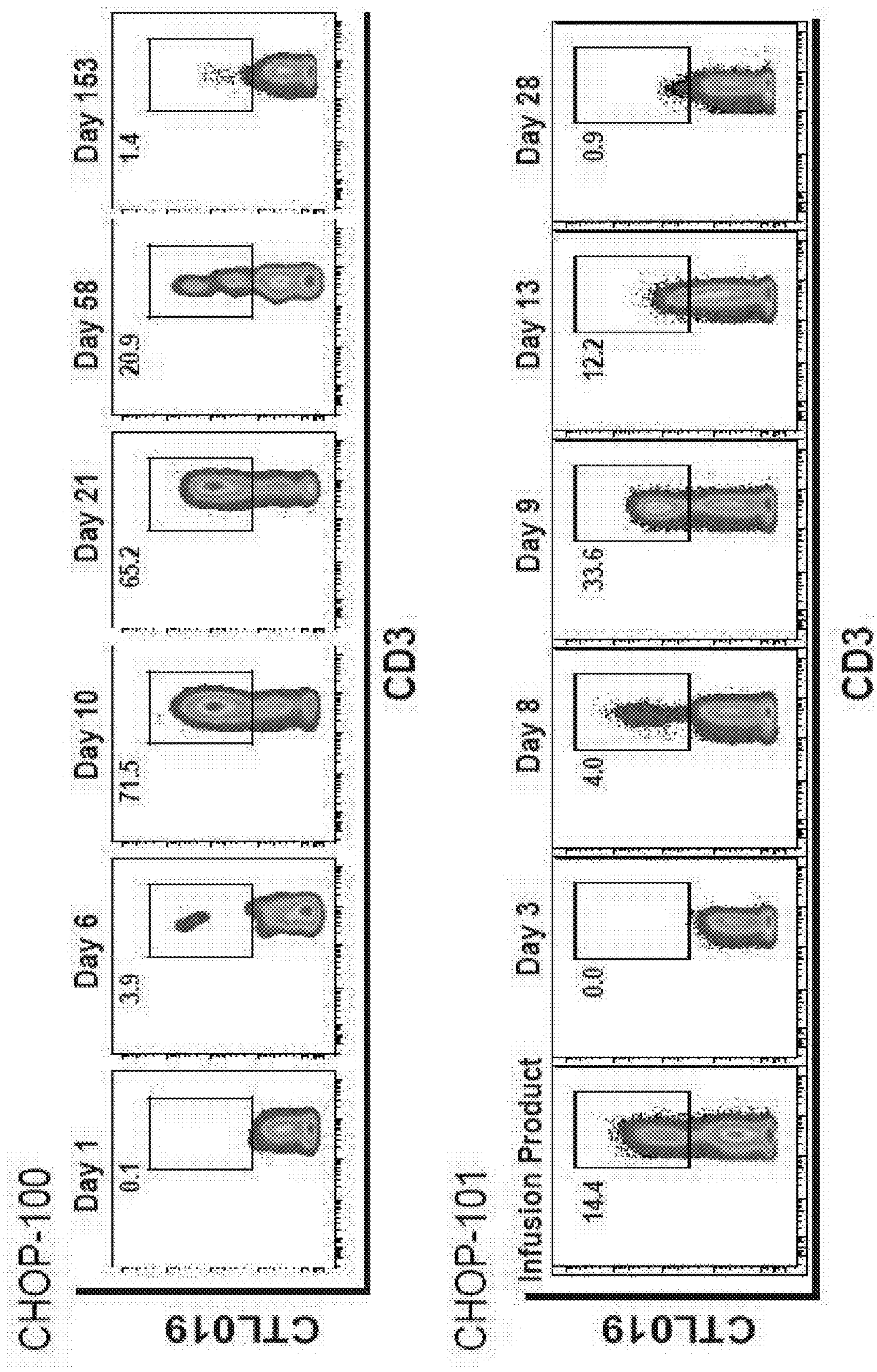
FIGS. 5A through 5D are images depicting expansion and visualization of CTL019 cells in peripheral blood, bone marrow and CSF.
Figure 6:
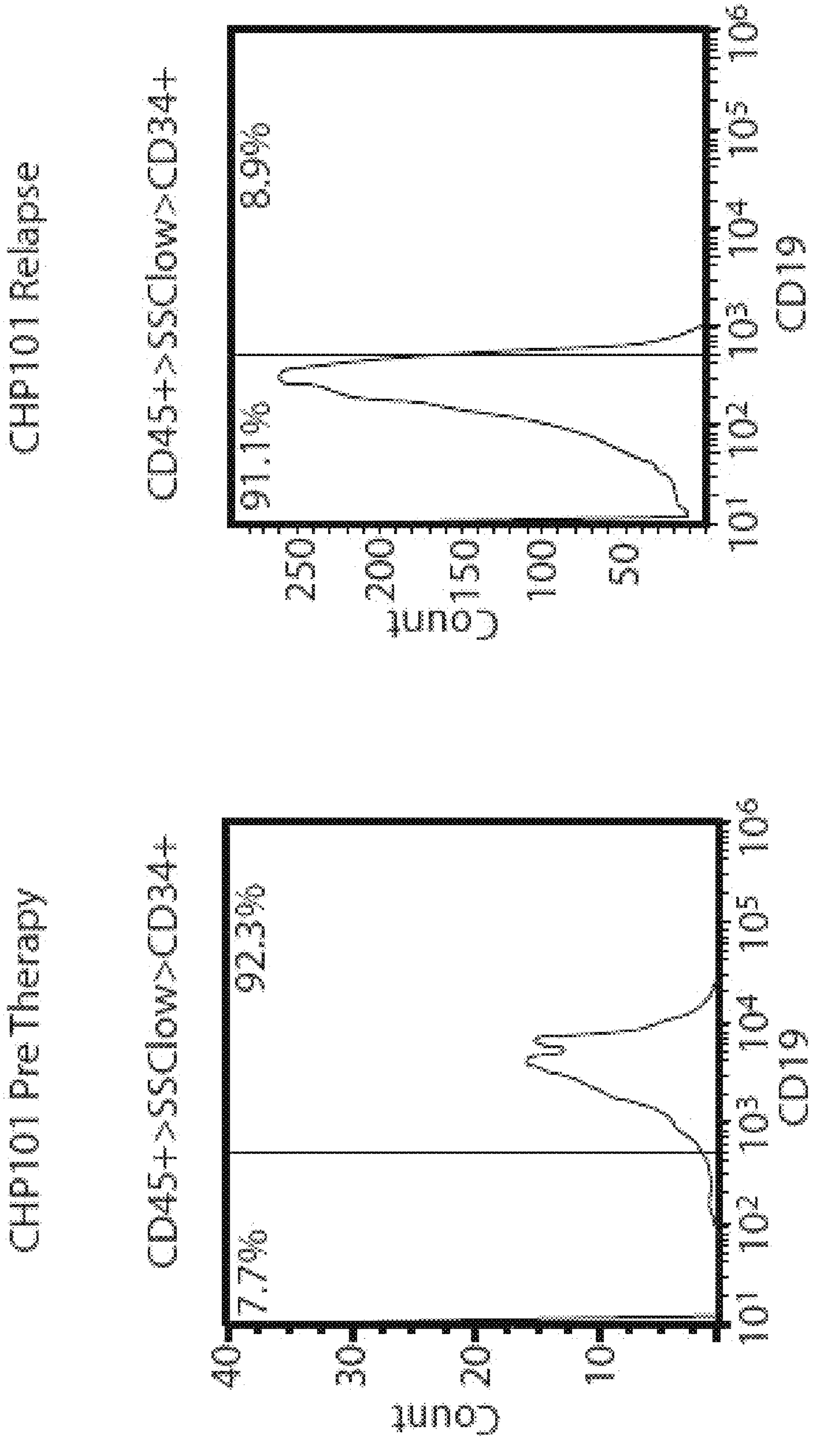
FIG. 6 is an image showing CD19 expression at baseline and at relapse in CHOP-101. Bone marrow samples from CHOP-101 were obtained prior to CTL019 infusion and at time of relapse 2 months later. Mononuclear cells isolated from marrow samples were stained for CD45, CD34 and CD19 and analyzed on an Accuri C6 flow cytometer. After gating on live cells, the blast gate (CD45+ SSC low) was subgated on CD34+ cells and histograms generated for CD19 expression. Division line represents threshold for the same gating on isotype controls. Pre-therapy blasts have a range of distribution of CD19, with a small population of very dim staining cells seen as the tail of the left histogram at 102 on the X-axis. The relapse sample does not have any CD19 positive blasts. Analysis of CD19 expression on the pre-treatment blast population revealed a small population of CD19 dim or negative cells. The mean fluorescence intensity (MFI) of this small population of cells was 187 (left panel), similar to the MFI of the anti-CD19-stained relapsed blast cells (201, right panel). Pre-therapy marrow sample was hypocellular with 10% blasts and relapse marrowsample was normocellular with 68% blasts, accounting for differences in events available for acquisition.
Figure 9A:
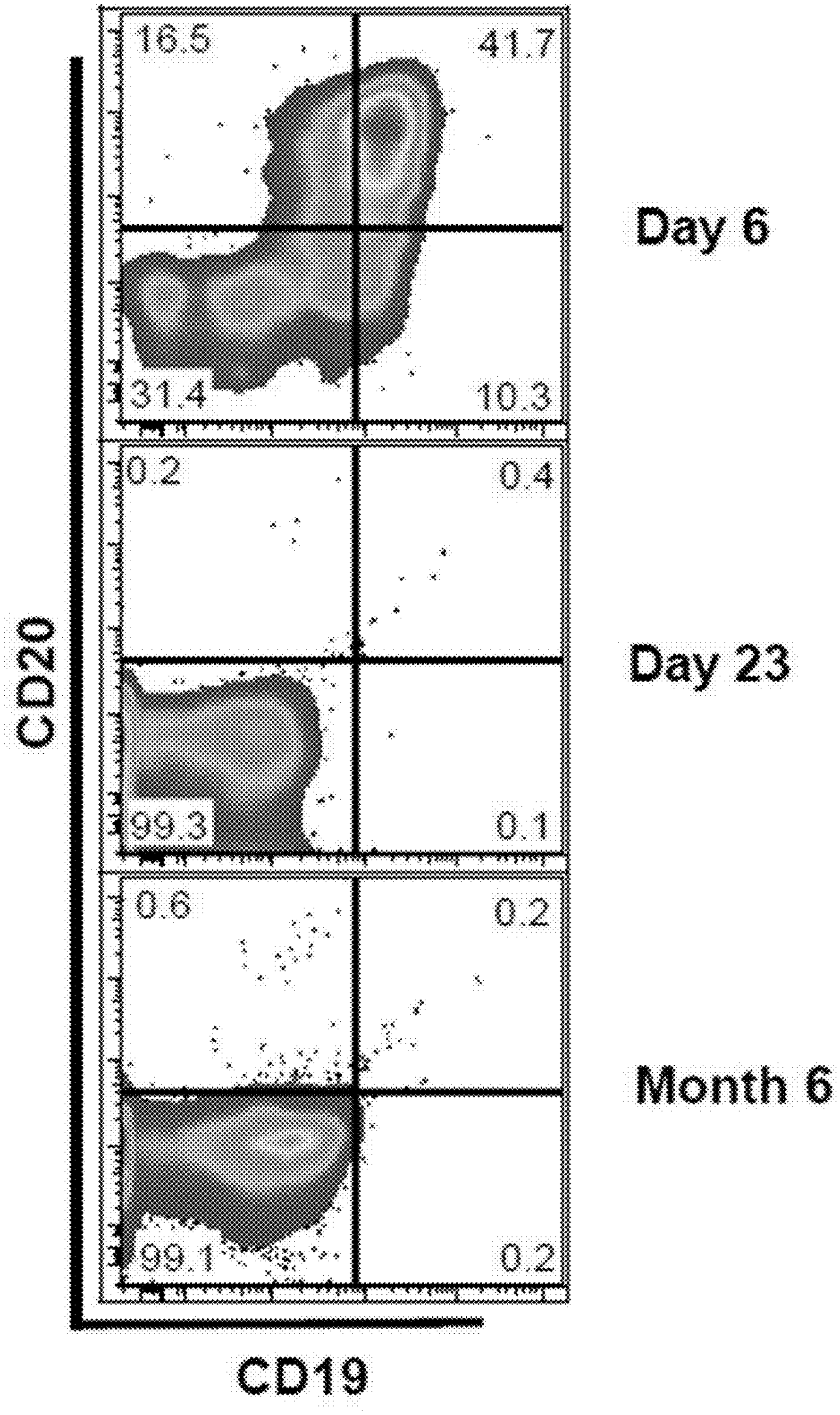
FIGS. 9A and 9B are images demonstrating that subjects had an elimination of CD19 positive cells in bone marrow and blood within 1 month after CTL019 infusion.
Figure 9B:
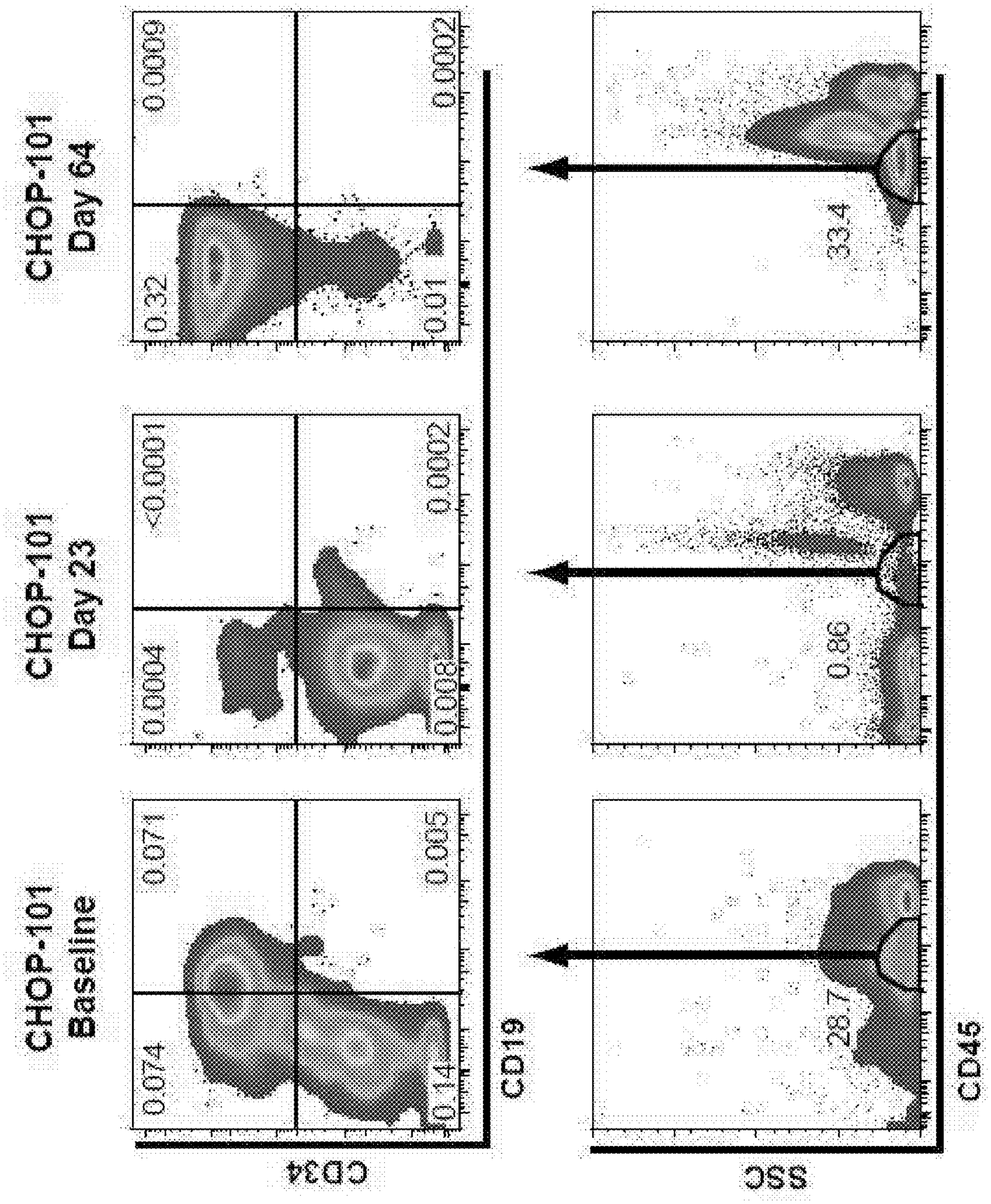

The fraction of CTL019 T cells in circulation progressively increased in vivo to 72% (CHOP-100) and 34% (CHOP-101) of T cells (FIG. 5A). The initial transduction efficiency was 11.6% and 14.4% in the T cells infused in CHOP-100 and -101, respectively. Given that the total ALC increased substantially in both patients (FIG. 4C), and that the frequency of CTL019 cells progressively increased in vivo from the baseline frequency (FIG. 8), there was a robust and selective expansion of CTL019 cells in both patients. The selective increase in T cells expressing CTL019 in both patients is consistent with an anti-leukemic mechanism involving CD19-driven expansion, and with the subsequent elimination of cells that express CD19 in both patients (FIG. 6 and FIGS. 9A-9B).

Molecular deep sequence analysis of TCRs in the peripheral blood and marrow samples in CHOP-100 obtained at D+23, when >65% of CD3+ cells in peripheral blood and marrow were shown to be CTL019+ by flow cytometry, revealed the absence of a dominant T cell TCR clonotype in either compartment, with the 10 most abundant T cells present at frequencies between 0.18-0.7% in bone marrow and 0.19 to 0.8% in peripheral blood. Six of the 10 dominant clones were shared between the two compartments. In addition both CD4 and CD8 CAR T cells are present. Thus, the CAR T cells appear to proliferate after CD19-stimulated expansion, and not by TCR signals or clone-specific events such as activation by integration of the lentivirus.

Trafficking and Morphology of CTL019 CAR T Cells in Marrow and CNS

Figure 5B:
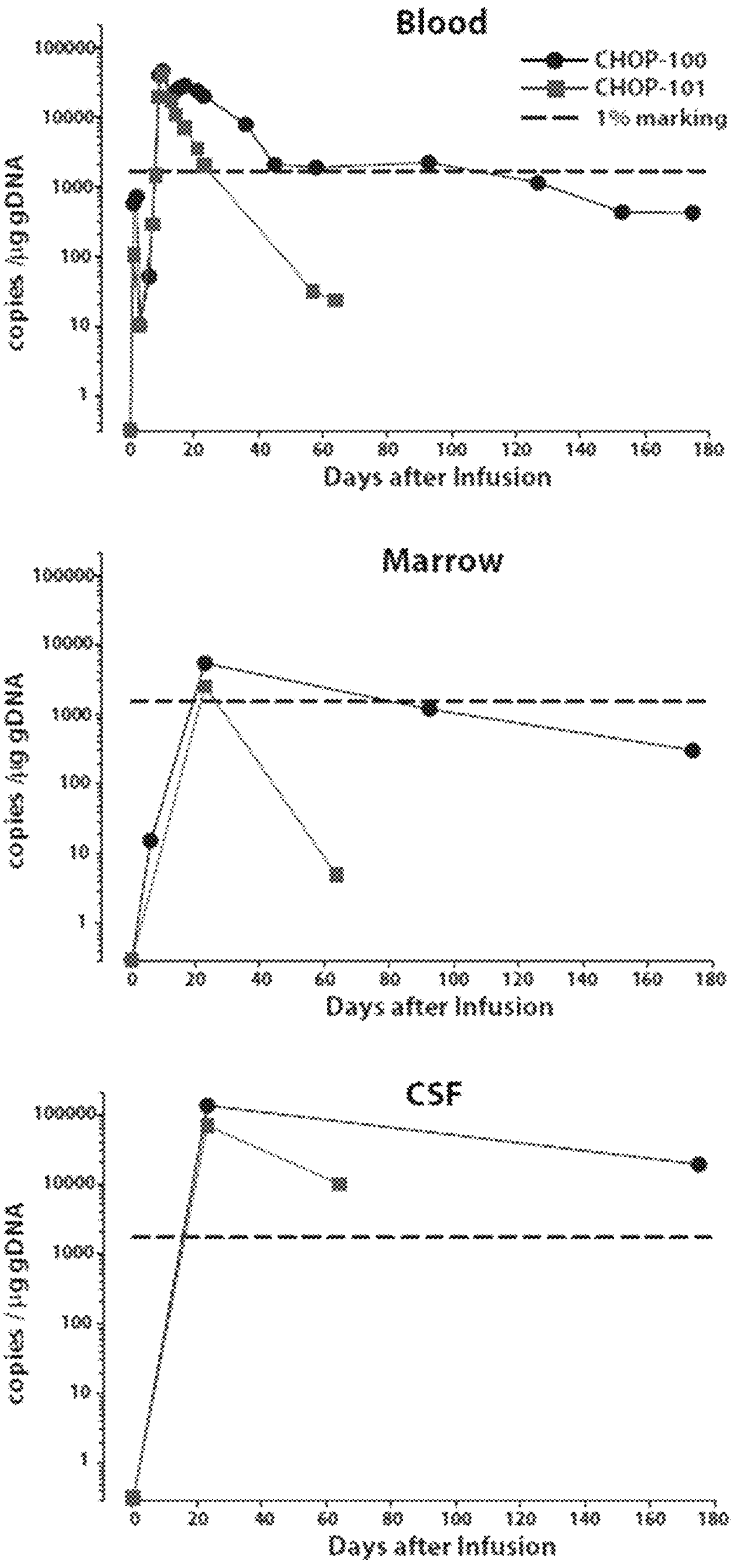
Figure 5C:
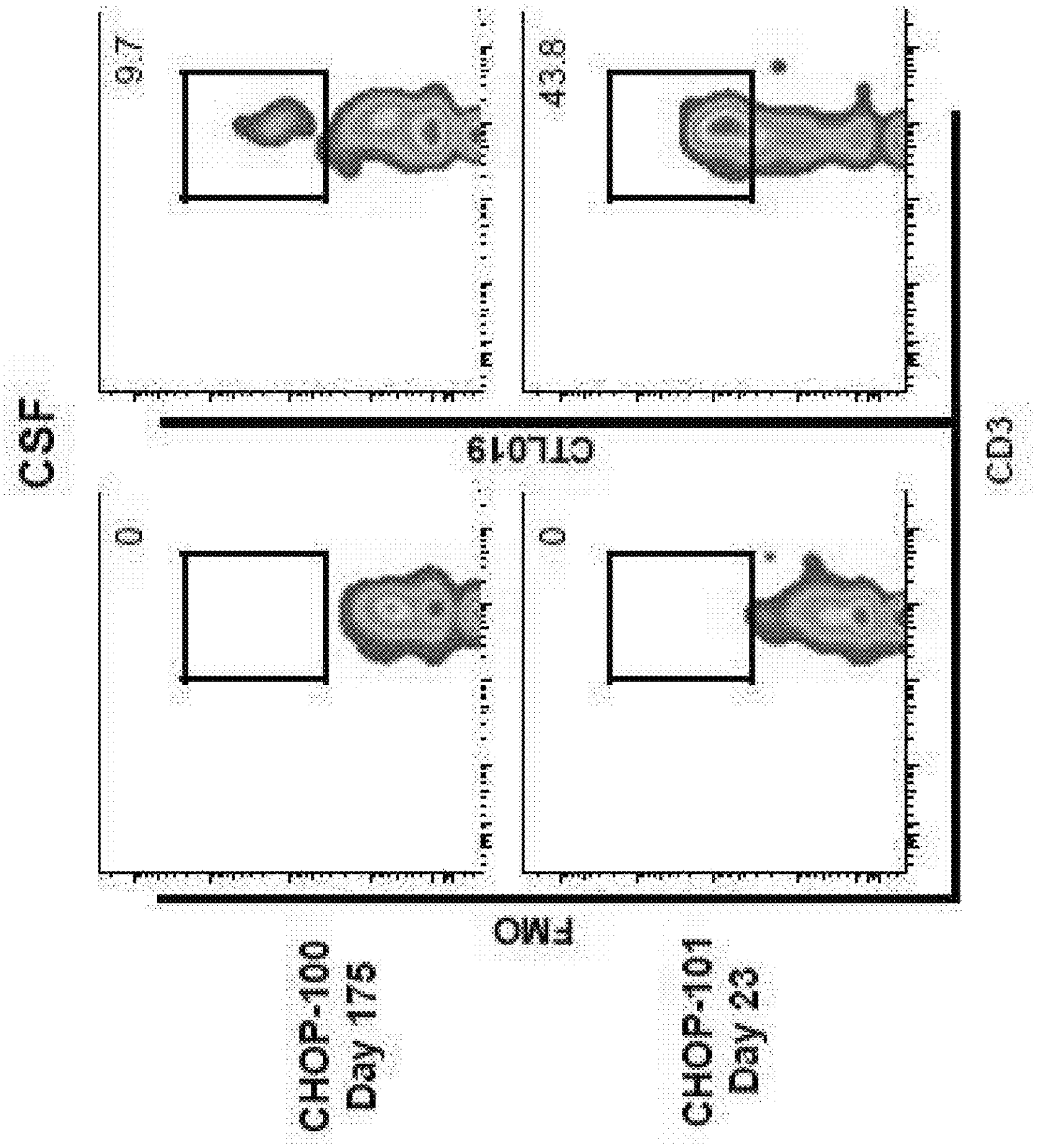
Figure 5D:
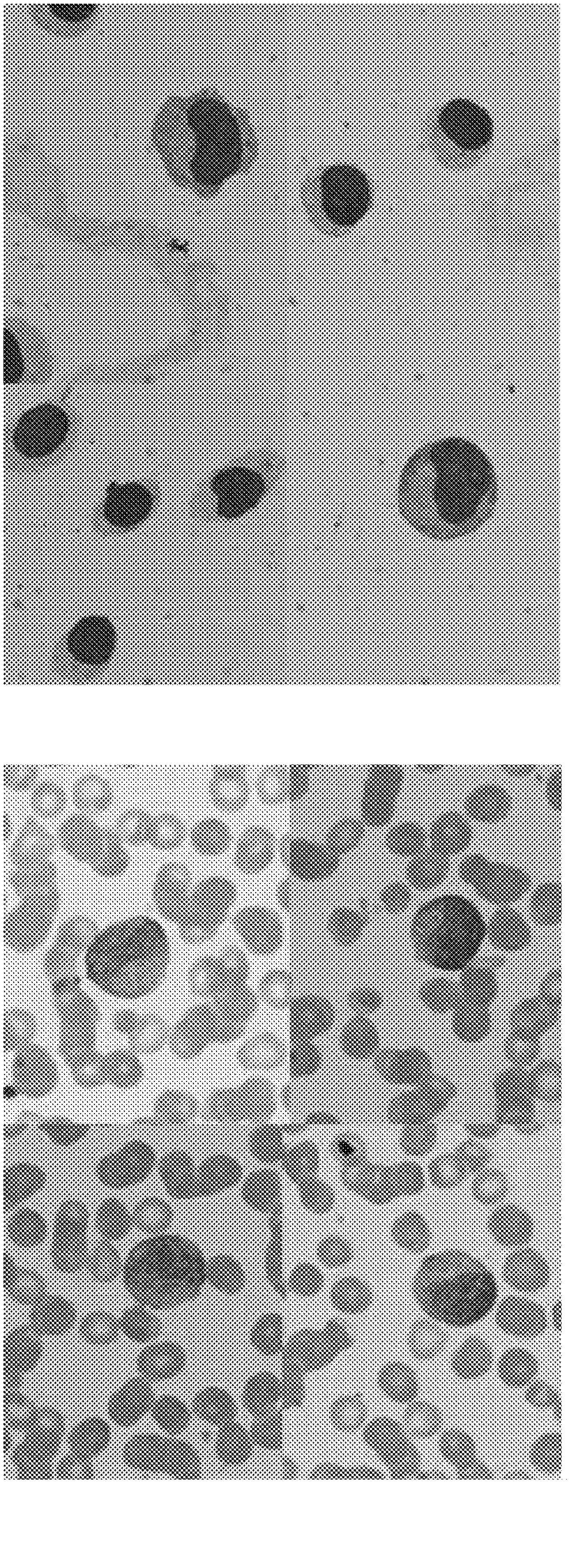

CTL019 cells expanded more than 1000-fold in the peripheral blood and bone marrow (FIGS. 5A-5D). The frequency of CTL019 cells increased to more than 10% of circulating T cells by D+20 in both subjects (FIG. 8), with the absolute magnitude of CTL019 expansion similar to that observed in patients with CLL (Kalos et al., 2011, Science Translational Medicine 3:95ra73). Unexpectedly, cells in the CSF also showed a high degree of CTL019 gene marking and also persisted at high frequency out to 6 months (FIG. 5B). The trafficking of CTL019 cells to the CSF was surprising given that neither patient had detectable CNS leukemia by cytospin at the time of infusion or at the 1 month post-treatment evaluation. Furthermore, prior reports of CAR therapy for B cell malignancies have not observed trafficking of CAR T cells to the CNS (Till et al., 2008, Blood 112:2261-71; Brentjens et al., 2011, Blood 118:4817-28; Savoldo et al., 2011, J Clin Invest 121:1822-5; Jensen et al., 2010, Biol Blood Marrow Transplant 16:1245-56; Till et al., 2012, Blood 119:3940-50; Kochenderfer et al., 2012, Blood 119:2709-20). The morphology of the lymphocytes in blood and CSF is shown for CHOP-100 and 101 in FIG. 5D. Since >70% of lymphocytes in circulation on D+10 were CTL019 cells (FIGS. 5A and 5B), most of the large granular lymphocytes shown in the left panel of FIG. 5D are likely CTL019 cells. Similarly, since many lymphocytes in the CSF obtained from CHOP-101 on D+23 were CTL019 cells (FIGS. 5B and 5C), the cytospin of CSF lymphocytes in FIG. 5D most likely represents the morphology of CTL019 cells in vivo that have trafficked to the CNS.

Induction of B Cell Aplasia

Both subjects had an elimination of CD19 positive cells in bone marrow and blood within 1 month after CTL019 infusion (FIG. 6, and FIG. 9). In CHOP-100, a large proportion of cells remaining in the marrow at D+6 after infusion were CD19+CD20+ leukemic blast cells. This population of cells was not detectable by D+23, an effect that is maintained beyond 9 months in this patient (FIGS. 9A-9B). Given that CHOP-100 did not have chemotherapy in the 6 weeks preceding CTL019 infusion, this indicates that CTL019 cells were sufficient to ablate normal and leukemic B cells in this case.

Emergence of CD19 Escape Variant in CHOP-101

CHOP-101 experienced a clinical relapse apparent in the peripheral blood at 2 months after CTL019 infusion, as evidenced by the reappearance of blast cells in the circulation. These cells were CD45dim positive, CD34 positive and did not express CD19 (FIG. 6). The absence of the original dominant CD34dim+CD34+CD19dim+ cells is consistent with a potent anti-leukemic selective pressure of the CTL019 CAR T cells directed to CD19 (FIG. 9B). Deep IGH sequencing revealed the presence of the malignant clone in peripheral blood and marrow as early as D+23 (Table 1), despite a clinical assessment of MRD negativity by flow cytometry at this timepoint (FIG. 7). In addition, deep sequencing of material obtained at clinical relapse revealed that the CD45dimCD34+CD19− cells are clonally related to the initial dominant CD45dim+CD34+CD19dim+ cells, since they share the same IGH sequence.

Remission of ALL by Chimeric Antigen Receptor-Expressing T Cells

The results presented herein demonstrate the induction of remission of relapsed and refractory leukemia in the first two patients treated on this protocol. Remission has been sustained in one subject and was accompanied by relapse due to the emergence of CD19 negative blasts in the other subject. Genetically modified CTL019 cells trafficked to the CNS at high levels in both patients. Cytokine elevations were observed that were on target, reversible, and temporally accompanied by elimination of blast cells that expressed CD19 in both subjects. The induction of complete remission in refractory CD19 positive ALL following infusion of CAR T cells is encouraging, particularly given the low frequency of remissions following the infusion of allogeneic donor lymphocyte infusions that do not express CARs (Kolb et al., 1995, Blood 86:2041-50; Collins et al., 1997, J Clin Oncol 15:433-44; Collins et al., 2000, Bone Marrow Transplant 26(5):511-6). Deep sequencing technology indicated that the CTL019 CAR infusion was associated with a sustained 5-log reduction in the frequency of malignant B cells in CHOP-100, further indicating potent antitumor effects in chemotherapy-refractory leukemia.

The unfortunate emergence of CD19-negative blast cells in one subject is consistent with previous reports that document the existence of CD19-negative precursor cells in some cases of ALL (Hotfilder et al., 2005, Cancer Research 65:1442-9; le Viseur et al., 2008, Cancer Cell 14:47-58). It is possible that the coinfusion of CAR T cells redirected to novel specificities in addition to CD19 might decrease the likelihood of this event. Thus far, relapse with CD19-negative escape cells in adults with CLL after treatment with CTL019 cells have not been observed (Kalos et al., 2011, Science Translational Medicine 3:95ra73), suggesting that this issue may be specific for a subset of acute leukemias. The induction of remission in CHOP-100 did not require concomitant chemotherapy, and is consistent with a previous report showing that remissions in CLL could be delayed for several weeks following chemotherapy (Porter et al., 2011, N Engl J Med 365:725-33). Thus, concomitant administration of cytotoxic chemotherapy may not be necessary for CAR-mediated antitumor effects.

Both pediatric ALL patients experienced substantial toxicity after CTL019 infusion. The induction of B-cell aplasia was observed, and indicates that the CAR T cells can function in the setting of relapsed acute leukemia. Both patients have also developed clinical and laboratory evidence of cytokine release syndrome and macrophage activation syndrome within a week of infusion. The cytokine profile observed in these patients is similar to prior reports of cytokine patterns in children with hemaphagocytosis and macrophage activation syndrome or hemophagocytic lymphohistiocytosis (Tang et al., 2008, Br J Haematol 143:84-91; Behrens et al., 2011, J Clin Invest 121(6):2264-77). Macrophage activation syndrome is characterized by hyper-inflammation with prolonged fever, hepatosplenomegaly, and cytopenias. Laboratory findings characteristic of this syndrome are elevated ferritin, triglycerides, transaminases, bilirubin (mostly conjugated) and soluble interleukin-2 receptor $\alpha$-chain, and decreased fibrinogen (Janka et al., 2012, Annu Rev Med 63:233-46). Recent studies indicate that tocilizumab (anti-IL6) has promise for glucocorticoid resistant GVHD (Drobyski et al., 2011, Biol Blood Marrow Transplant 17(12):1862-8; Le Huu et al., 2012, J Invest Dermatol 132(12):2752-61; Tawara et al., 2011, Clinical Cancer Research 17:77-88), and the results presented herein are consistent with these data.

The vigorous in vivo expansion of CTL019, persistent B-cell aplasia and prominent anti-leukemia activity imply substantial and sustained effector functions of the CTL019 cells in pediatric patients with advanced ALL. The high efficiency of trafficking of CAR T cells to the CNS is encouraging as a mechanism for surveillance to prevent relapse in a sanctuary site such as the CNS (Pullen et al., 1993, J Clin Oncol 11(5):839-49), and supports the testing of CAR T-cell-directed therapies for CNS lymphomas and primary CNS malignancies. With the exception of B-cell aplasia, the duration of which is currently undefined, it is believed that the use of immune-based therapies such as CTL019 may have a favorable profile of long-term adverse effects compared to the high doses of chemotherapy and radiation that are employed as the current standard of care for most cases of pediatric leukemia (Garcia-Manero and Thomas, 2001, Hematol Oncol Clin North Am 15(1):163-205).

Induction of Complete Remissions of ALL by Chimeric Antigen Receptor-Expressing T Cells Tocilizumab (anti-IL6) has promise for glucocorticoid resistant GVHD, and the results presented herein are consistent with these data. Further, it is interesting to note that in CHOP 100, the CRS manifesting as high fever, hypotension and multi-organ failure was resistant to the high doses of glucocorticoids administered over the previous 2 days before cytokine directed therapy. Finally, in CHOP-100 the biphasic changes in IL-1β, IL-1RA and IL-2 shown in FIG. 4B may have been related to cytokine-directed therapy with etanercept and tocilizumab.

The induction of remission in a patient refractory to blinatumomab therapy further highlights the potency of CTL019 cells. The high efficiency of trafficking of CAR T cells to the CNS is encouraging as a mechanism for surveillance to prevent relapse in a sanctuary site such as the CNS, and supports the testing of CAR T-cell-directed therapies for CNS lymphomas and primary CNS malignancies. Neither patient has experienced cognitive effects that might be ascribed to the trafficking of T cells to the CNS.

Example 4: Summary Information

Figure 10:
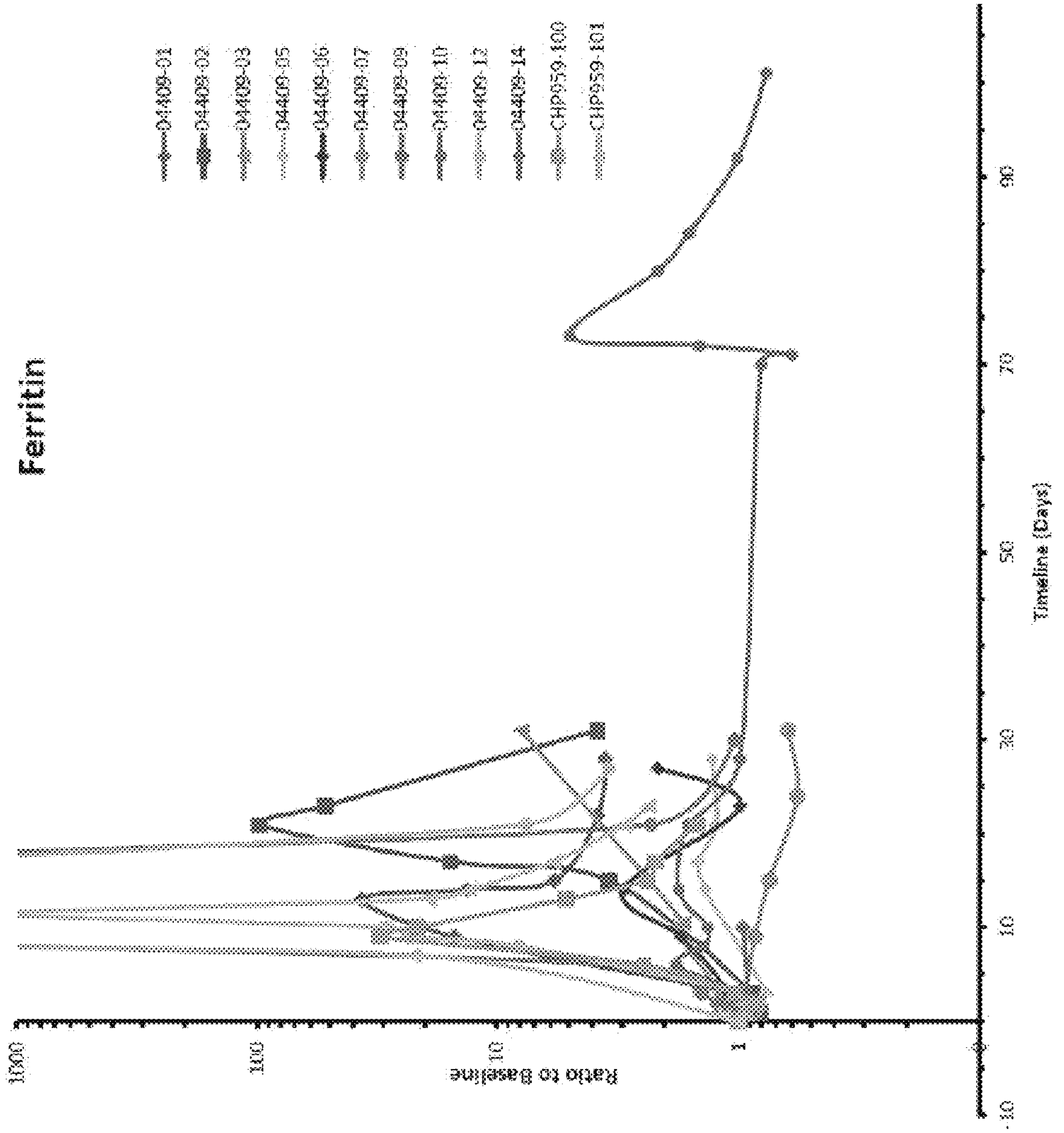
FIG. 10 is a graph depicting the levels of ferritin present in the patient following receipt of CAR T cells.
Figure 11:
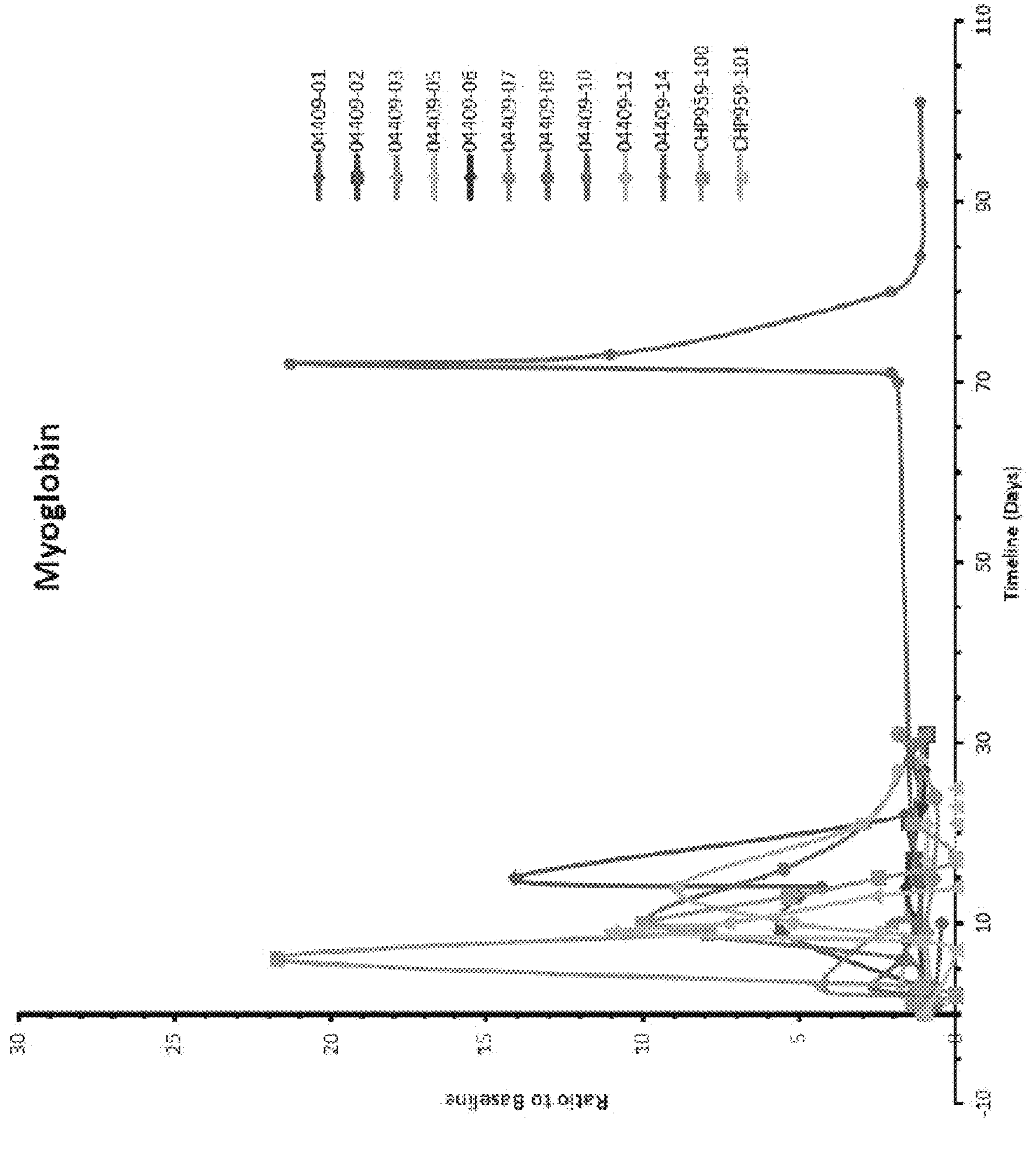
FIG. 11 is a graph depicting the levels of myoglobin present in the patient following receipt of CAR T cells.
Figure 12:
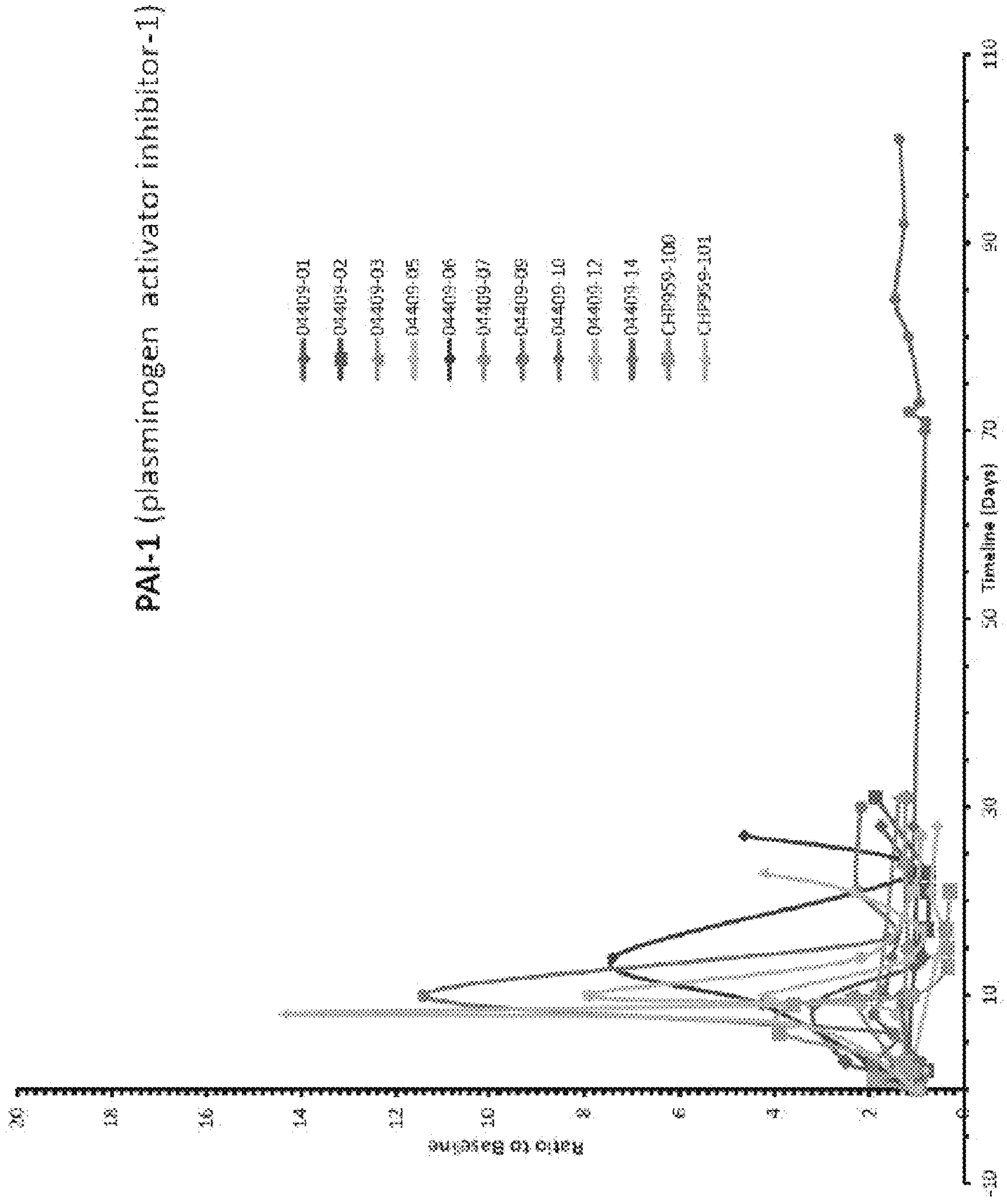
FIG. 12 is a graph depicting the levels of plasminogen activator inhibitor-1 (PAI-1) present in the patient following receipt of CAR T cells.

Various markers were measured in patients receiving CAR T cells. As a non-limiting example, Ferritin, Myoglobin, and plasminogen activator inhibitor-1 (PAI-1) were measure; see FIGS. 10, 11 and 12, respectively. Elevated levels of these markers correlated with outcome. Patients designated as −01, −03, −09, −100 and −101 were classified as complete responders. Patients designated as −02, −05, −10 (second infusion and response around D70) and −12 were classified as partial responders. Patient designated as −06, −07 and −14 were classified as non-responders.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING

```
Sequence total quantity: 1
SEQ ID NO: 1            moltype = AA  length = 242
FEATURE                 Location/Qualifiers
source                  1..242
                        mol_type = protein
                        organism = synthetic construct
SEQUENCE: 1
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SS                                                                242
```

The invention claimed is:

1. A method of ameliorating cytokine toxicity occurring following administration of a T cell genetically modified to express a chimeric antigen receptor (CAR) to a patient, the method comprising administering tocilizumab to the patient after the administration of the T cell genetically modified to express the CAR, wherein the CAR comprises a CD19 antigen binding domain, a transmembrane domain, a costimulatory signaling region, and a CD3 zeta signaling domain, wherein:

(i) the CD19 antigen binding domain comprises the light chain variable region and the heavy chain variable region of SEQ ID NO: 1; and (ii) the costimulatory signaling region comprises a 4-1BB signaling domain or a CD28 signaling domain, thereby ameliorating the cytokine toxicity in the patient.

2. The method of claim 1, wherein the patient has a hematological cancer.

3. The method of claim 2, wherein the hematological cancer is leukemia or lymphoma.

4. The method of claim 2, wherein the hematological cancer is pre-B ALL (pediatric indication), adult ALL, mantle cell lymphoma, diffuse large B-cell lymphoma, or non-Hodgkin's lymphoma.

5. The method of claim 1, wherein the costimulatory signaling region comprises a 4-1BB signaling domain.

6. The method of claim 1, wherein the costimulatory signaling region comprises a CD28 signaling domain.

* * * * *